(12) United States Patent
Shimizu

(10) Patent No.: US 10,906,139 B2
(45) Date of Patent: Feb. 2, 2021

(54) JOINING METHOD

(71) Applicant: OLYMPUS CORPORATION, Tokyo (JP)

(72) Inventor: Tomokazu Shimizu, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 143 days.

(21) Appl. No.: 16/212,786

(22) Filed: Dec. 7, 2018

(65) Prior Publication Data

US 2019/0105741 A1    Apr. 11, 2019

Related U.S. Application Data

(63) Continuation of application No. PCT/JP2017/020475, filed on Jun. 1, 2017.

(30) Foreign Application Priority Data

Jun. 15, 2016 (JP) ................... 2016-119077

(51) Int. Cl.
  *B23P 11/02* (2006.01)
  *F16B 4/00* (2006.01)
  *A61N 7/00* (2006.01)

(52) U.S. Cl.
  CPC .............. *B23P 11/025* (2013.01); *A61N 7/00* (2013.01); *B23P 11/02* (2013.01); *F16B 4/00* (2013.01); *F16B 4/008* (2013.01)

(58) Field of Classification Search
  CPC ..... A61M 37/0092; A61M 29/00; A61N 7/00; B23P 11/02; B23P 11/025; F16B 2/00;
  (Continued)

(56) References Cited

U.S. PATENT DOCUMENTS 3,046,649 A * 7/1962 Brennan ................. B23P 11/02
228/131
3,345,732 A * 10/1967 Brower ................. B21D 26/14
29/419.2

(Continued)

FOREIGN PATENT DOCUMENTS

JP    S57194832 A    11/1982
JP    S59159409 A    9/1984

(Continued)

OTHER PUBLICATIONS

International Search Report dated Sep. 5, 2017 issued in PCT/JP2017/020475.

*Primary Examiner* — Lawrence Averick
(74) *Attorney, Agent, or Firm* — Scully, Scott, Murphy & Presser, P.C.

(57) ABSTRACT

A joining method of joining two pieces of subjects to be joined together, the subjects being a first member and a second member that has a joint insertion portion in which the first member is inserted, the method including: heating the second member that is set in an expansion restricting member and in which the first member is inserted to the joint insertion portion to first temperature to cause the second member to have thermal expansion and thereby causing the joint insertion portion to have plastic deformation in a direction in which a diameter shrinks with mechanically restricting thermal expansion of the second member by an inner surface of the expansion restricting member; and cooling the second member after the heating to join the first member and the second member together.

11 Claims, 18 Drawing Sheets

(58) Field of Classification Search
CPC .......... F16B 1/0014; F16B 4/00; F16B 4/008; A61B 17/22; A61B 17/225; A61H 23/00
See application file for complete search history.

(56) References Cited

U.S. PATENT DOCUMENTS 4,598,857 A * 7/1986 Matsui ................. B23K 20/001
156/86
2012/0180299 A1 7/2012 Sharp

FOREIGN PATENT DOCUMENTS

| | | | |
|---|---|---|---|
| JP | S59159409 U | * | 10/1984 |
| JP | S59202117 A | | 11/1984 |
| JP | S61037318 A | | 2/1986 |
| JP | H08155746 A | | 6/1996 |
| WO | 2011005125 A2 | | 1/2011 |

* cited by examiner

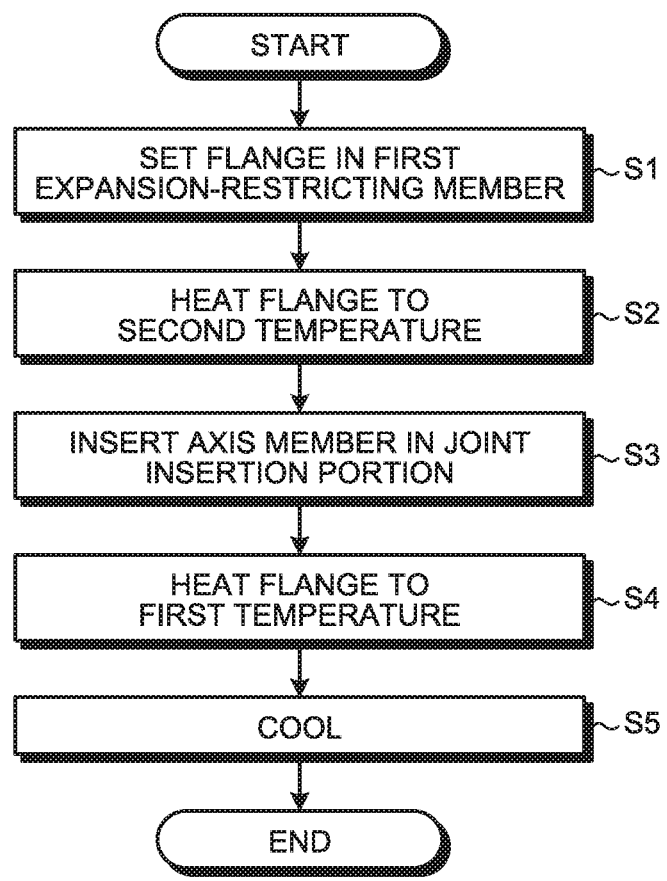

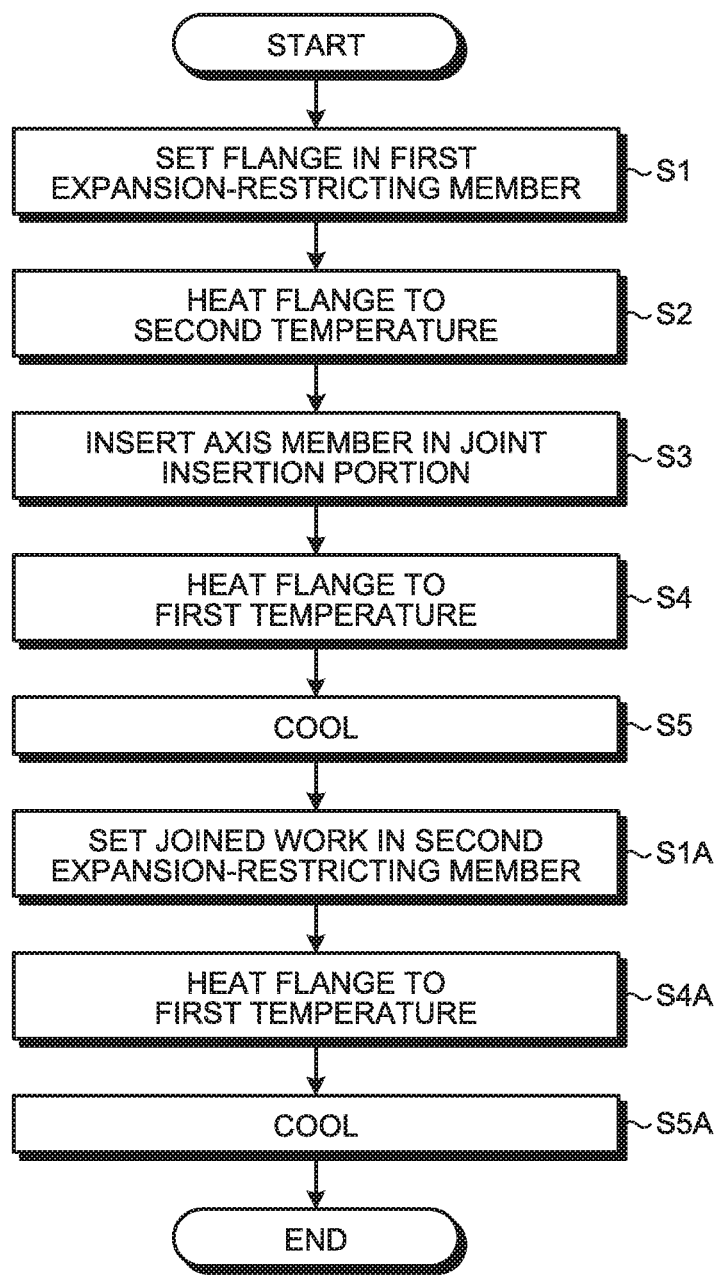

JOINING METHOD

CROSS REFERENCES TO RELATED APPLICATIONS

This application is a continuation of PCT international application Ser. No. PCT/JP2017/020475 filed on Jun. 1, 2017 which designates the United States, incorporated herein by reference, and which claims the benefit of priority from Japanese Patent Applications No. 2016-119077, filed on Jun. 15, 2016, incorporated herein by reference.

BACKGROUND

1. Technical Field

The present disclosure relates to a joining method of joining two pieces of subjects to be joined together by shrink fitting.

2. Related Art

In the related art, shrink fitting has been known as a method of joining two pieces of subjects to be joined, a first member and a second member having a joint insertion portion into which the first member is inserted, with each other (for example, refer to International Publication Pamphlet No. 2011/005125).

The shrink fitting is a technique of joining pieces by using diameter shrink of the joint insertion portion that occurs when it is cooled, by heating the second member in advance to cause thermal expansion to expand the diameter of the joint insertion portion, and then inserting the first member therein in this diameter-expanded state.

In the technique disclosed in International Publication Pamphlet No. 2011/005125, to improve joint strength of subjects to be joined, a rough surface region is provided on a joint surface of the subjects to be joined, and then the shrink fitting described above is performed.

SUMMARY

In some embodiments, provided is a joining method of joining two pieces of subjects to be joined together, the subjects being a first member and a second member that has a joint insertion portion in which the first member is inserted. The method includes: heating the second member that is set in an expansion restricting member and in which the first member is inserted to the joint insertion portion to first temperature to cause the second member to have thermal expansion and thereby causing the joint insertion portion to have plastic deformation in a direction in which a diameter shrinks with mechanically restricting thermal expansion of the second member by an inner surface of the expansion restricting member; and cooling the second member after the heating to join the first member and the second member together.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a flowchart showing a joining method of two pieces of subjects to be joined by using the joining apparatus shown in FIG. 3A and FIG. 3B;

FIG. 14 is a flowchart showing a joining method according to a second embodiment;

DETAILED DESCRIPTION

Figure 1:
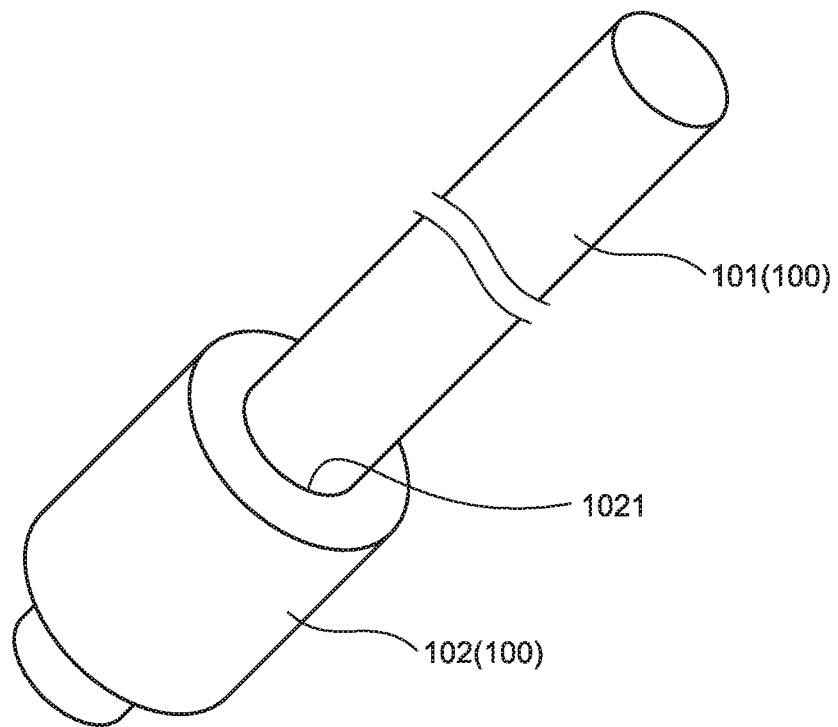
FIG. 1 is a diagram showing two pieces of subjects to be joined according to a first embodiment.

Forms to implement the disclosure (hereinafter, embodiments) are explained, referring to the drawings. The embodiments explained below are not intended to limit the disclosure. Furthermore, like reference symbols are assigned to like parts throughout the drawings.

First Embodiment

Structure of Subjects to be Joined

Figure 2:
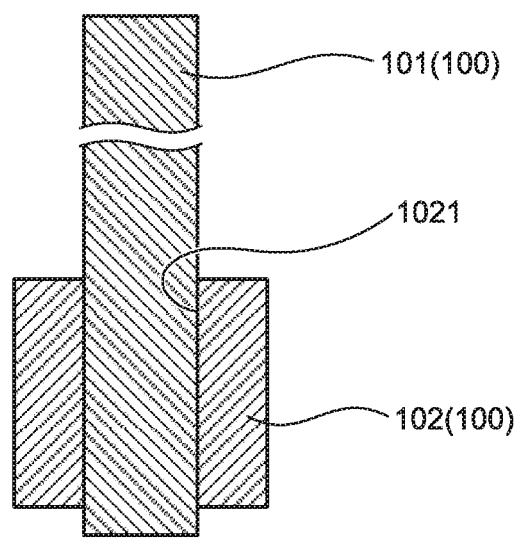
FIG. 2 is a diagram showing two pieces of subjects to be joined according to the first embodiment.

FIG. 1 and FIG. 2 are diagrams showing two pieces of subjects to be joined 100 according to a first embodiment. Specifically, FIG. 1 is a perspective view of the two pieces of subjects to be joined 100. FIG. 2 is a cross section of the two pieces of subjects to be joined 100 taken along a center axis of the two pieces of subjects to be joined 100. FIG. 1 and FIG. 2 show a state in which the subjects to be joined 100 are joined together for convenience of explanation.

The two pieces of subjects to be joined 100 are constituted of an axis member 101 and a flange 102 as shown in FIG. 1 or FIG. 2.

The axis member 101 corresponds to a first member according to the disclosure, and is constituted of a long, substantially cylindrical member as shown in FIG. 1 or FIG. 2. The axis member 101 is, for example, made from a titanium alloy, or the like.

The flange 102 corresponds to a second member according to the disclosure, and is formed in a substantially cylindrical shape having a joint insertion portion 1021 (FIG. 1, FIG. 2) in which the axis member 101 is inserted. The flange 102 is for example, made from an aluminum alloy (linear expansion coefficient α: approximately $25\times10^{-6}/C.°$) or the like.

The axis member 101 and the flange 102 explained above are joined together in a state in which the axis member 101 is inserted in the joint insertion portion 1021 as shown in FIG. 1 or FIG. 2.

The axis member 101 and the flange 102 joined together are used, for example, for ultrasound treatment equipment to treat a tissue of a living body by applying an ultrasonic energy to the tissue of the living body. Specifically, the axis member 101 and the flange 102 joined together are used as a probe that transmits ultrasonic vibration generated by an ultrasonic transducer from one end (an end portion on a lower side in FIG. 1 and FIG. 2) to the other end (an end portion on an upper side in FIG. 1 and FIG. 2) that comes in contact with the tissue of the living body.

Structure of Joining Apparatus

Next, a structure of a joining apparatus 1 that join the subjects to be joined 100 together is explained.

Figure 3A:
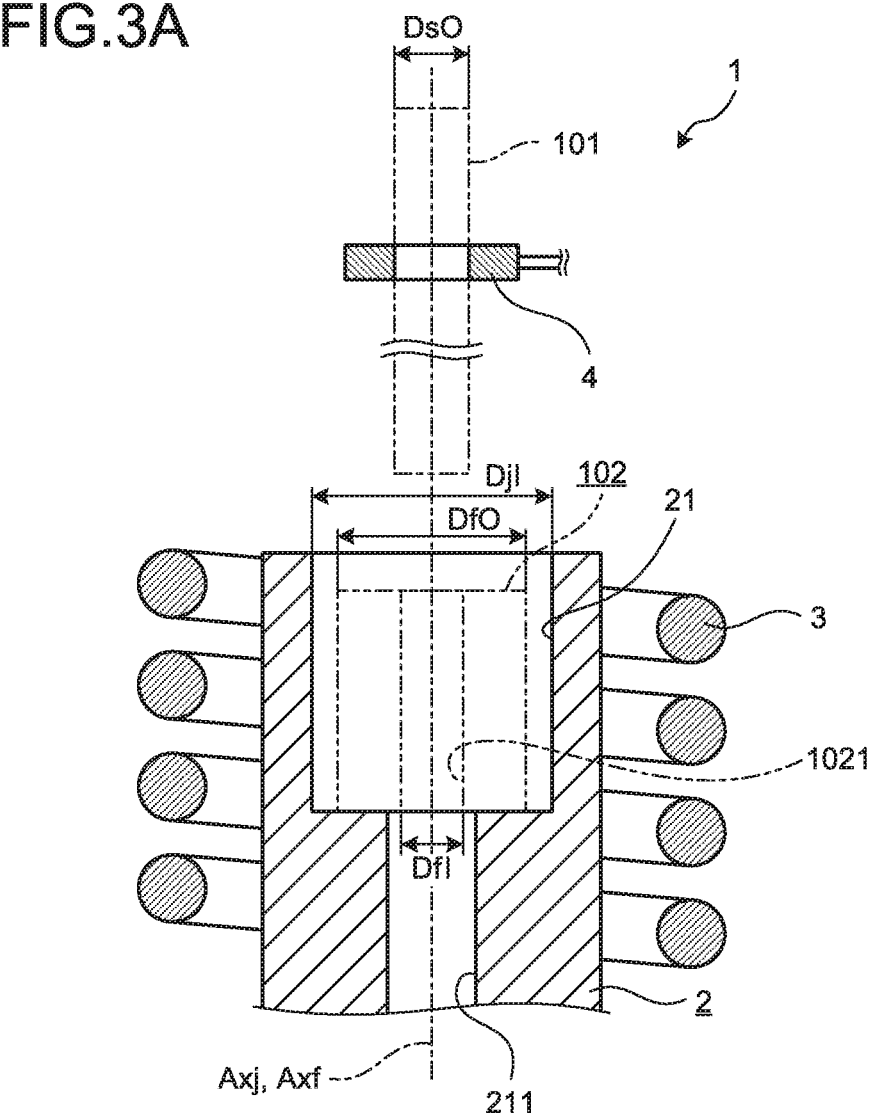
FIG. 3A is a diagram showing a joining apparatus according to the first embodiment.
Figure 3B:
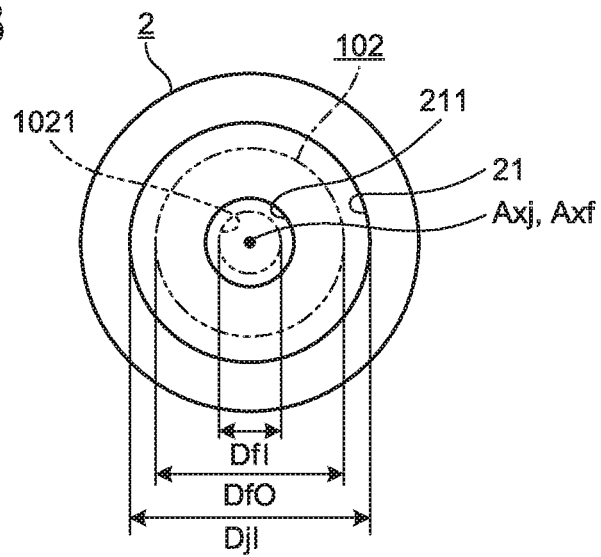
FIG. 3B is a diagram showing the joining apparatus according to the first embodiment.

FIG. 3A and FIG. 3B is a diagram showing the joining apparatus 1. Specifically, FIG. 3A is a cross section of the joining apparatus 1 viewed from a side. FIG. 3B is a top view of the joining apparatus 1. In FIG. 3B, illustration of an electromagnetic-induction heating coil 3 and an axis-member holding unit 4 is omitted for convenience of explanation.

The joining apparatus 1 includes a first expansion-controlling member 2, the electromagnetic-induction heating coil 3 (FIG. 3A), and the axis-member holding unit 4 (FIG. 3A) as shown in FIG. 3A or FIG. 3B.

The first expansion-restricting member 2 corresponds to an expansion restricting member according to the disclosure, and is constituted of a cylindrical member that extends along a vertical axis as shown in FIG. 3A or FIG. 3B. The first expansion-restricting member 2 is, for example, made from Kovar (linear expansion coefficient β: approximately $5\times10^{-6}/C.°$), or the like. That is, the first expansion-restricting member 2 is made from a material, the linear expansion coefficient β of which is smaller than the linear expansion coefficient α of the flange 102.

In this first expansion-restricting member 2, a recessed portion 21 in a circular shape in a planar view recessed toward a lower end portion is formed at an upper end portion as shown in FIG. 3A or FIG. 3B. An inner diameter size Djl of this recessed portion 21 is set to be larger than an outer diameter size DfO of the flange 102 at room temperature. Moreover, a height size of the recessed portion 21 (height size in a direction along a center axis Axj of the first expansion-restricting member 2) is set to be larger than a height size of the flange 102 (a length size in a direction along a center axis Axf of the flange 102 in a cylindrical shape).

This recessed portion 21 is a portion in which the flange 102 is inserted to be set at a bottom portion of the recessed portion 21. That is, the recessed portion 21 corresponds to a setting insertion portion according to the disclosure.

Furthermore, at the bottom portion of the recessed portion 21, an insertion hole 211 to avoid a mechanical interference of the axis member 101 and the bottom portion is formed.

The electromagnetic-induction heating coil 3 is wound on an outer peripheral surface of the first expansion-restricting member 2 keeping predetermined intervals. The electromagnetic-induction heating coil 3 is supplied with a high frequency current from a high-frequency power source (not shown), thereby induction heating the first expansion-restricting member 2.

The axis-member holding unit 4 holds the axis member 101, and is enabled to move (for example, move three-dimensionally) the axis member 101.

Joining Method

Next, a joining method of the subjects to be joined 100 together by using the joining apparatus 1 is explained.

FIG. 4 is a flowchart showing the joining method of the subjects to be joined 100 together by using the joining apparatus 1. FIG. 5A, FIG. 5B, FIG. 6A, FIG. 6B, FIG. 7A, FIG. 7B, FIG. 8A, FIG. 8B, FIG. 9A, and FIG. 9B are diagrams explaining the joining method shown in FIG. 4. Specifically, FIG. 5A, FIG. 6A, FIG. 7A, FIG. 8A, and FIG. 9A are diagrams corresponding to FIG. 3A. FIG. 5B, FIG. 6B, FIG. 7B, FIG. 8B, and FIG. 9B are diagrams corresponding to FIG. 3B. FIG. 10 is a diagram showing changes of the inner diameter size Djl of the recessed portion 21, the outer diameter size DfO of the flange 102, and an inner diameter size Dfl of the joint insertion portion 1021 when the joining method shown in FIG. 4 is performed.

In the joining method explained below, the change in the outer diameter size DsO (FIG. 3A, FIG. 3B) of the axis member 101 caused by the thermal expansion of the axis member 101 is determined as "0 (no change)" (FIG. 10) because it is small compared to the changes of the other sized Djl, DfO, Dfl. Moreover, in FIG. 10, as the inner diameter size Djl of the recessed portion 21, that before performing the joining method (at room temperature) is defined as an inner diameter size DjlB, that after completion of the joining method (at room temperature) is defined as an inner diameter size DjlA. As the outer diameter size DfO of the flange 102 also, that before performing the joining method (at room temperature) is defined as an outer diameter size DfOB, and that after completion of the joining method (at room temperature) is defined as an outer diameter size DfOA. Furthermore, as the inner diameter size Dfl of the joint insertion portion 1021 also, that before performing the joining method (at room temperature) is defined as an inner diameter size DflB, and that after completion of the joining method (at room temperature) is defined as an inner diameter size DflA. Moreover, in the joining method explained below, the outer diameter size DsO of the axis member 101 before performing the joining method (at room temperature) is larger than the inner diameter size Dfl (DflB) of the joint insertion portion 1021 as shown in FIG. 10.

Figure 5A:
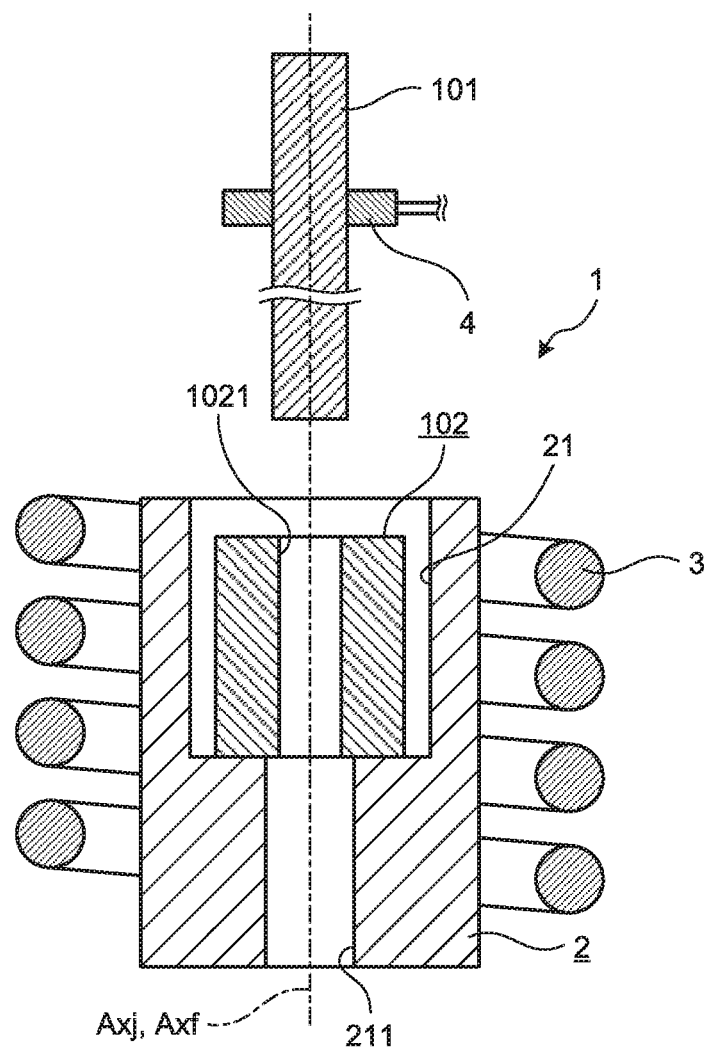
FIG. 5A is a diagram explaining the joining method (second-member setting step) shown in FIG. 4.
Figure 5B:
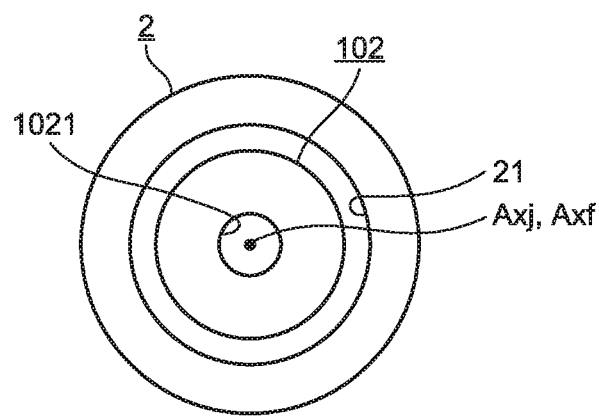
FIG. 5B is a diagram explaining the joining method (second-member setting step) shown in FIG. 4.

First, an operator sets the flange 102 in the first expansion-restricting member 2 (the recessed portion 21) such that the center axis Axj of the first expansion-restricting member 2 (the recessed portion 21) and the center axis Axf of the flange 102 coincide with each other (step S1: second-member setting step) as shown in FIG. 5A or FIG. 5B. In this state, because it is at room temperature and the inner diameter size Djl (DjlB) of the recessed portion 21 is larger than the outer diameter size DfO (DfOB) of the flange 102 as described above, there is a gap between the inner peripheral surface of the recessed portion 21 and the outer peripheral surface of the flange 102 as shown in FIG. 5A or FIG. 5B. Moreover, the operator sets the axis member 101 on the axis-member holding unit 4 (FIG. 5A).

Next, the operator supplies high frequency current to the electromagnetic-induction heating coil 3 from the high-frequency power source (not shown), to induction-heat the first expansion-restricting member 2 (step S2: pre-joining heating step). The temperature of flange 102 set in the recessed portion 21 increases as heat is transferred from the first expansion-restricting member 2.

Figure 6A:
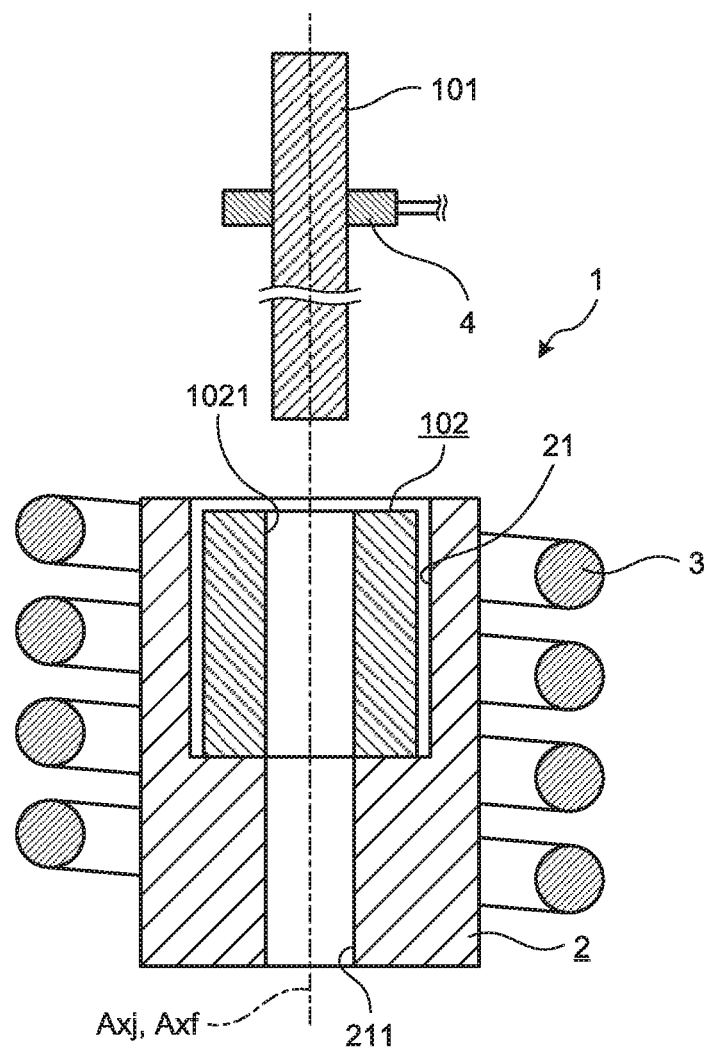
FIG. 6A is a diagram explaining the joining method (pre-joining heating step) shown in FIG. 4.
Figure 6B:
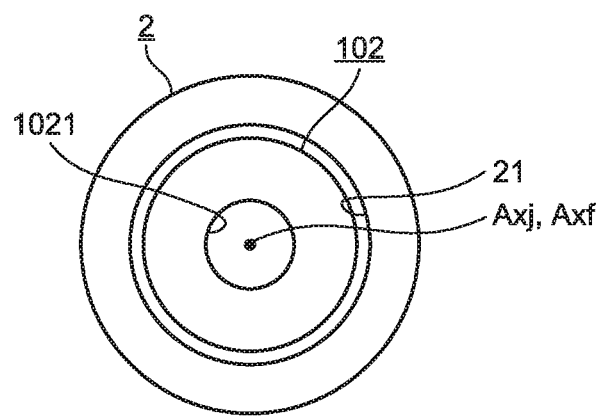
FIG. 6B is a diagram explaining the joining method (pre-joining heating step)

By performing this step S2, thermal expansion occurs in the first expansion-restricting member 2 and the flange 102 (FIG. 6A, FIG. 6B). The inner diameter size Djl of the recessed portion 21, the outer diameter size DfO of the flange 102, and the inner diameter size Dfl of the joint insertion portion 1021 gradually increase as shown in FIG. 10.

As described above, the linear expansion coefficient $\beta$ of the first expansion-restricting member 2 is smaller than the linear expansion coefficient $\alpha$ of the flange 102. Therefore, the change of the outer diameter size DfO of the flange 102 is larger than that of the inner diameter size Djl of the recessed portion 21 as shown in FIG. 10. On the other hand, because the inner diameter size Dfl of the joint insertion portion 1021 is smaller than the outer diameter size DfO of the flange 102, it changes mildly compared to the outer diameter size DfO.

At step S2, the operator continues to heat the first expansion-restricting member 2 by induction heating until the flange 102 reaches second temperature T2. The second temperature T2 is temperature at which the inner diameter size Dfl of the joint insertion portion 1021 becomes larger than the outer diameter size DsO of the axis member 101.

Figure 7A:
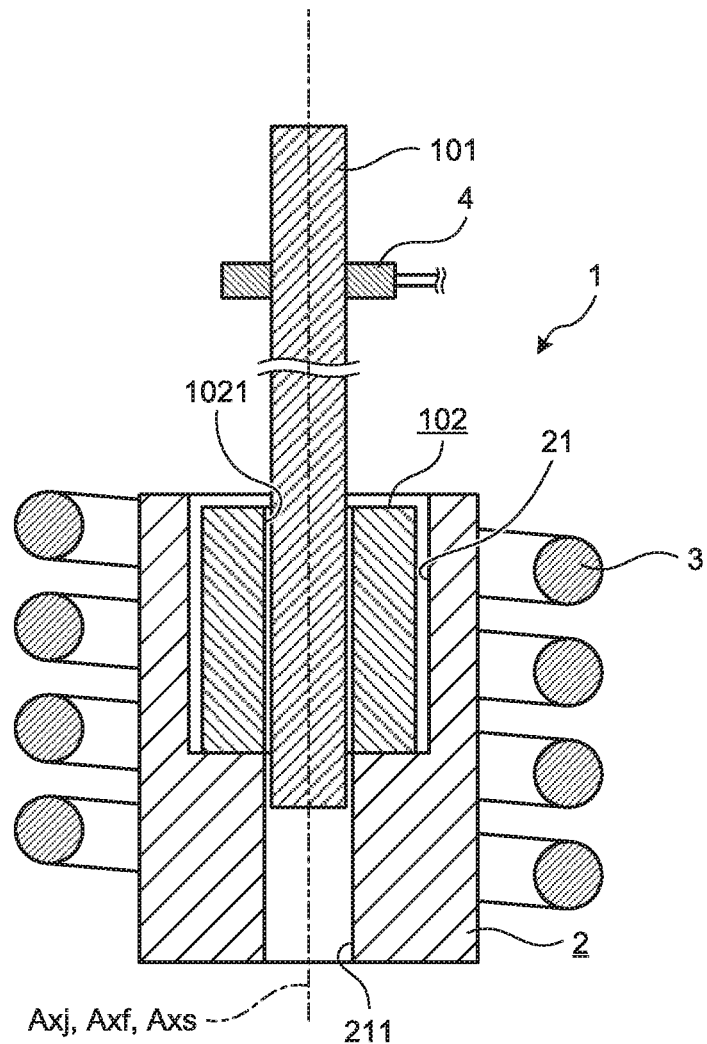
FIG. 7A is a diagram explaining the joining method (first-member inserting step) shown in FIG. 4.
Figure 7B:
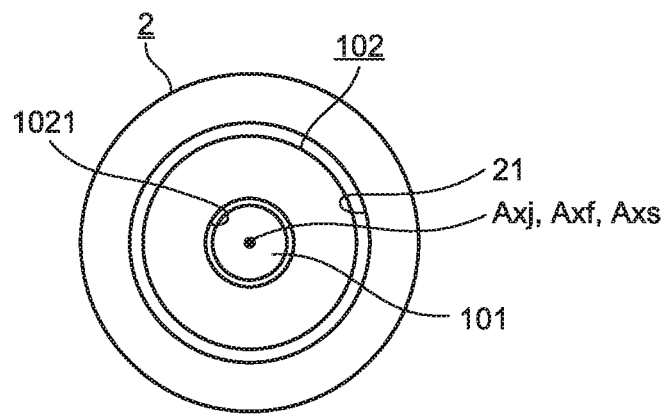
FIG. 7B is a diagram explaining the joining method (first-member inserting step) shown in FIG. 4.

Next, the operator stops the supply of high frequency current to the electromagnetic-induction heating coil 3 from the high-frequency power source (not shown) (stops induction heating of the first expansion-restricting member 2 (heating of the flange 102), and operates the axis-member holding unit 4 to insert the axis member 101 in the joint insertion portion 1021 such that the center axis Axf of the flange 102 and the center axis Axs of the axis member 101 coincide with each other (step S3: first-member inserting step). At this time, in the axis member 101, the end portion on the lower side protruding from the joint insertion portion 1021 is inserted through the insertion hole 211 as shown in FIG. 7A.

Next, the operator supplies high frequency current to the electromagnetic-induction heating coil 3 from the high-frequency power source (not shown), and heats the first expansion-restricting member 2 by induction heating until the flange 102 reaches first temperature T1 (step S4: additional heating step). The first temperature T1 is temperature higher than the second temperature T2 as shown in FIG. 10.

When the flange 102 is heated to the first temperature T1 at this step S4, the flange 102 acts as follows.

Figure 8A:
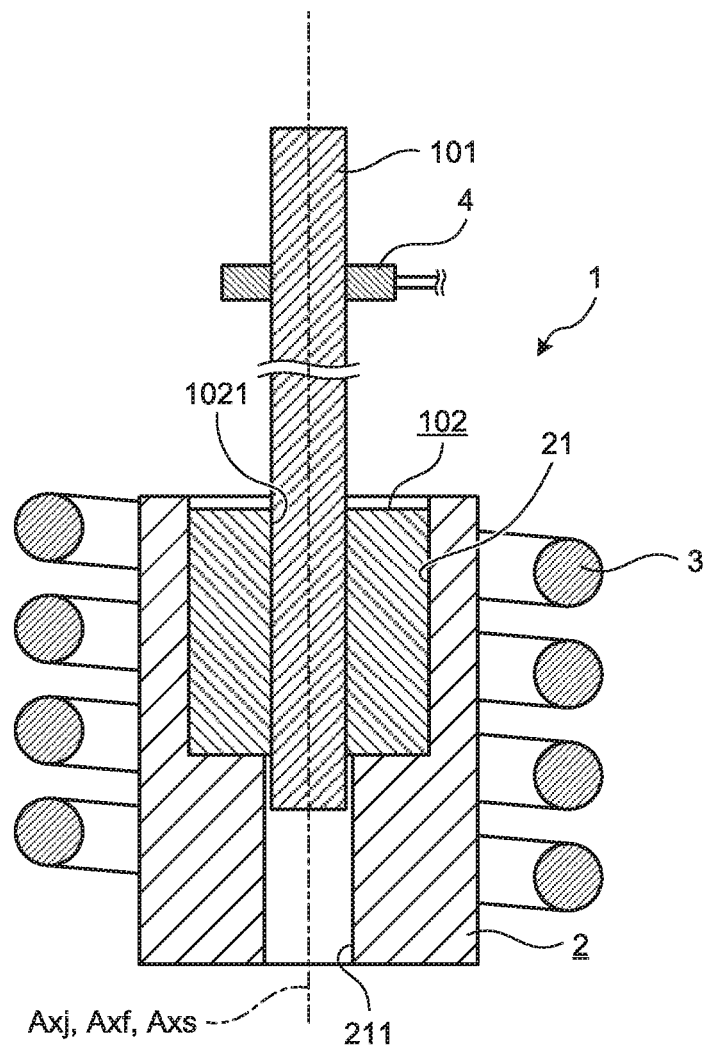
FIG. 8A is a diagram explaining the joining method (additional heating step) shown in FIG. 4.
Figure 8B:
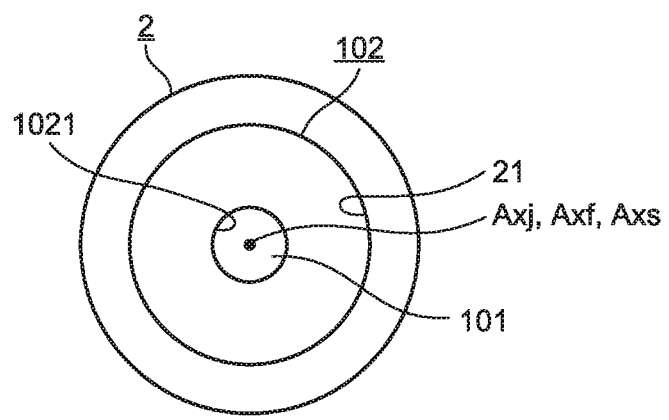
FIG. 8B is a diagram explaining the joining method (additional heating step) shown in FIG. 4.

Specifically, the flange 102 and the first expansion-restricting member 2 expand as shown in FIG. 8A, FIG. 8B, or FIG. 10 by thermal expansion. Due to the difference between the linear expansion coefficients $\alpha$, $\beta$ of the flange 102 and the first expansion-restricting member 2, the inner diameter size Djl of the recessed portion 21 and the outer diameter size DfO of the flange 102 become the same (the inner peripheral surface of the recessed portion 21 abuts on the outer peripheral surface of the flange 102) at a point when it reaches expansion restricting temperature Tx (temperature lower than the first temperature T1 (FIG. 10)).

Thereafter, in the course of the temperature of the flange 102 becoming higher than the expansion restricting temperature Tx, the flange 102 continues thermal expansion but expansion of the flange 102 is mechanically restricted by the inner peripheral surface of the recessed portion 21. Therefore, the flange 102 makes plastic deformation in a direction not restricted mechanically by the recessed portion 21, that is, a height direction, and in a direction in which the inner diameter size Dfl of the joint insertion portion 1021 shrinks. The inner diameter size Dfl of the joint insertion portion 1021 gradually decreases once it exceeds the expansion restricting temperature Tx as shown in FIG. 10. Moreover, the shrink of the diameter of the joint insertion portion 1021 is mechanically restricted by the outer peripheral surface of the axis member 101. That is, the inner diameter size Dfl of the joint inserting portion 1021 becomes the same as the outer diameter size DsO of the axis member 101 eventually.

Next, the operator stops the supply of high frequency current to the electromagnetic-induction heating coil 3 from the high-frequency power source (not shown) (stops induction heating of the first expansion-restricting member 2 (heating of the flange 102)), and cools the first expansion-restricting member 2 and the flange 102 to room temperature (step S5: cooling step).

Figure 9A:
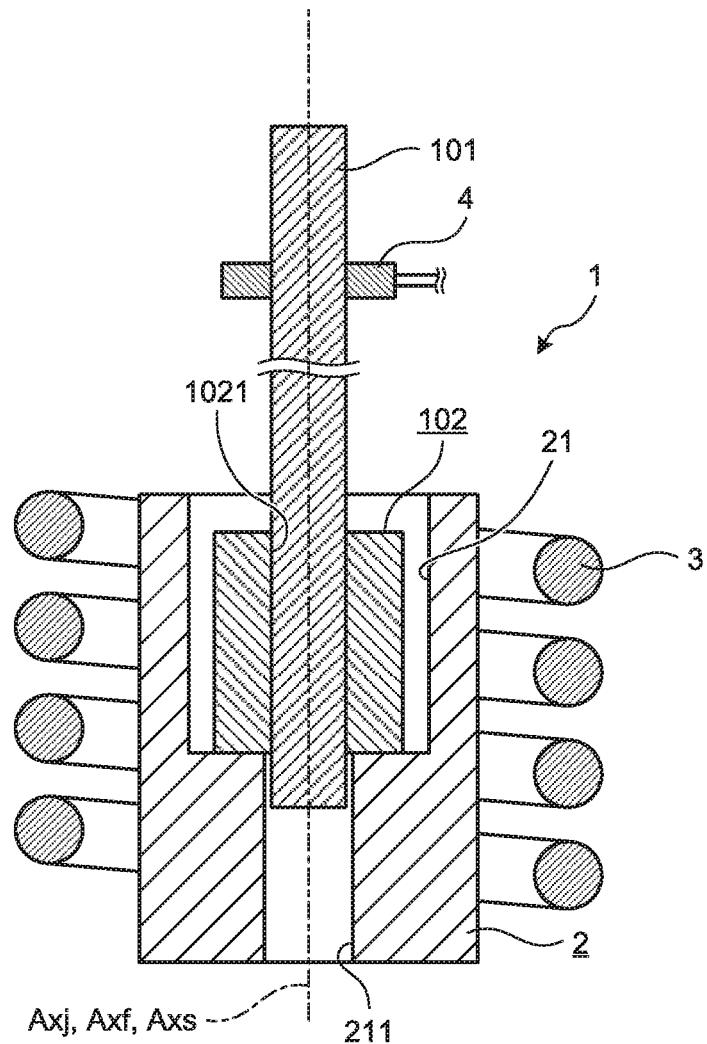
FIG. 9A is a diagram explaining the joining method (cooling step) shown in FIG. 4.
Figure 9B:
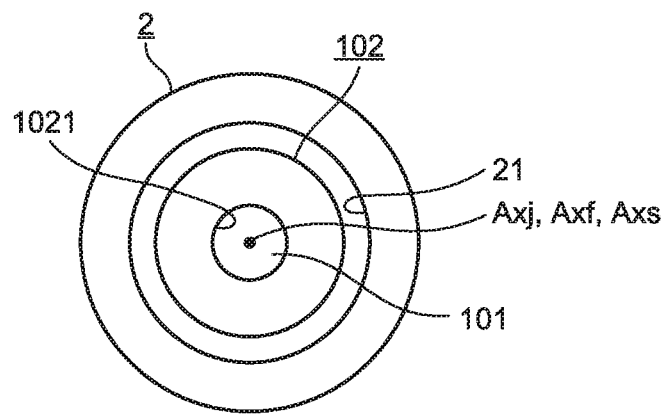
FIG. 9B is a diagram explaining the joining method (cooling step) shown in FIG. 4.
Figure 10:
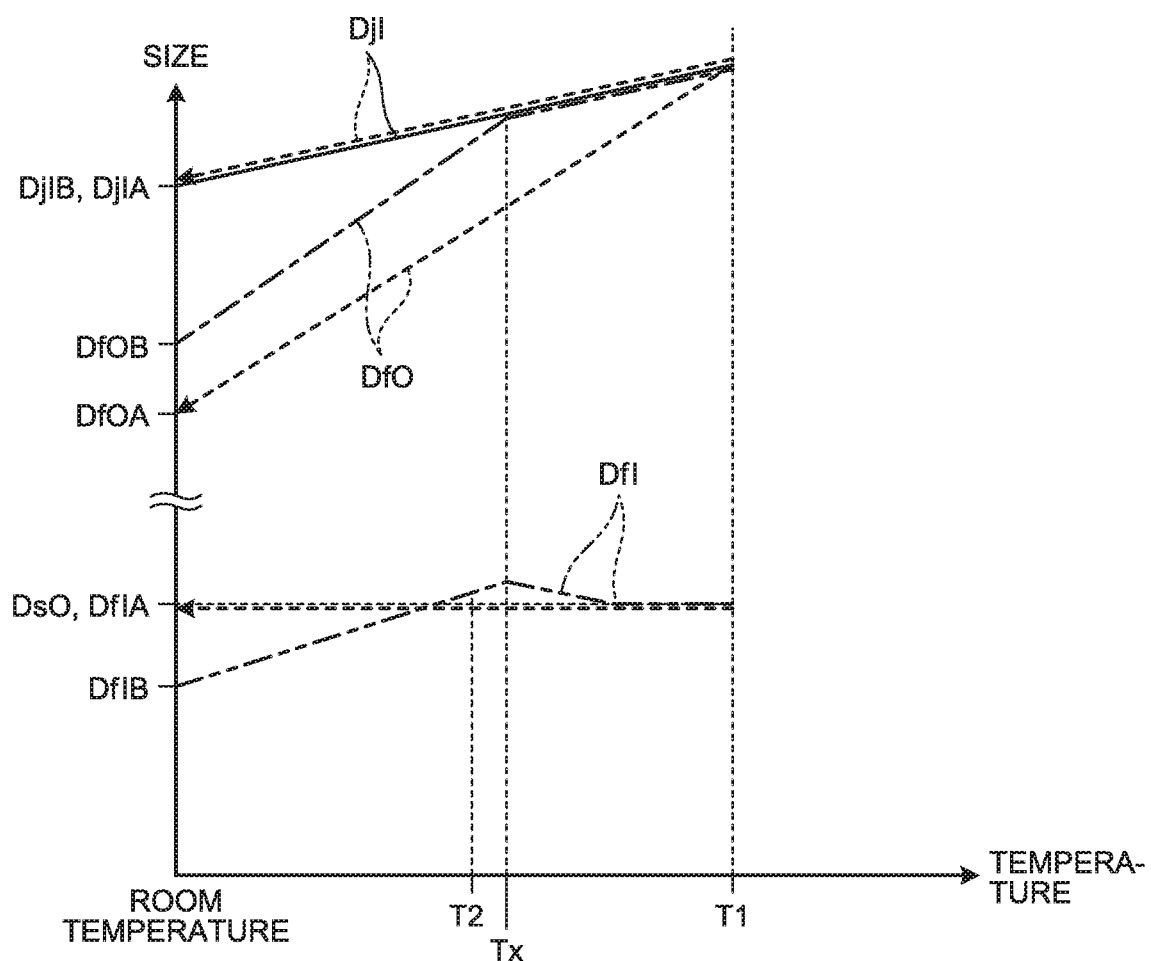
FIG. 10 is a diagram showing changes in an inner diameter size of a recessed portion, an outer diameter size of a flange, and an inner diameter size of a joint insertion portion when the joining method shown in FIG. 4 is performed.

By the cooling at this step S5, the flange 102 and the first expansion-restricting member 2 contract as shown in FIG. 9A, FIG. 9B, or FIG. 10. Specifically, the inner diameter size Djl of the recessed portion 21 gradually decreases in response to contraction of the first expansion-restricting member 2 as indicated by a broken line arrow in FIG. 10, and becomes the inner diameter size DjlA same as the inner diameter size DjlB before performing the joining method in the end. Furthermore, the outer diameter size DfO of the flange 102 gradually decreases in response to contraction of the flange 102 as indicated by a broken line arrow in FIG. 10, and becomes the outer diameter size DfOA smaller than the outer diameter size DfOB before performing the joining method in the end. Moreover, the joint insertion portion 1021 tries to decrease the inner diameter size Dfl gradually in response to contraction of the flange 102, but keeps the inner diameter size DflA that matches with the outer diameter size DsO of the axis member 101 in the end because the contraction is restricted mechanically by the outer peripheral surface of the axis member 101.

By the above steps, the axis member 101 and the flange 102 are joined together.

The joining method according to the first embodiment explained above produces a following effect.

Figure 11:
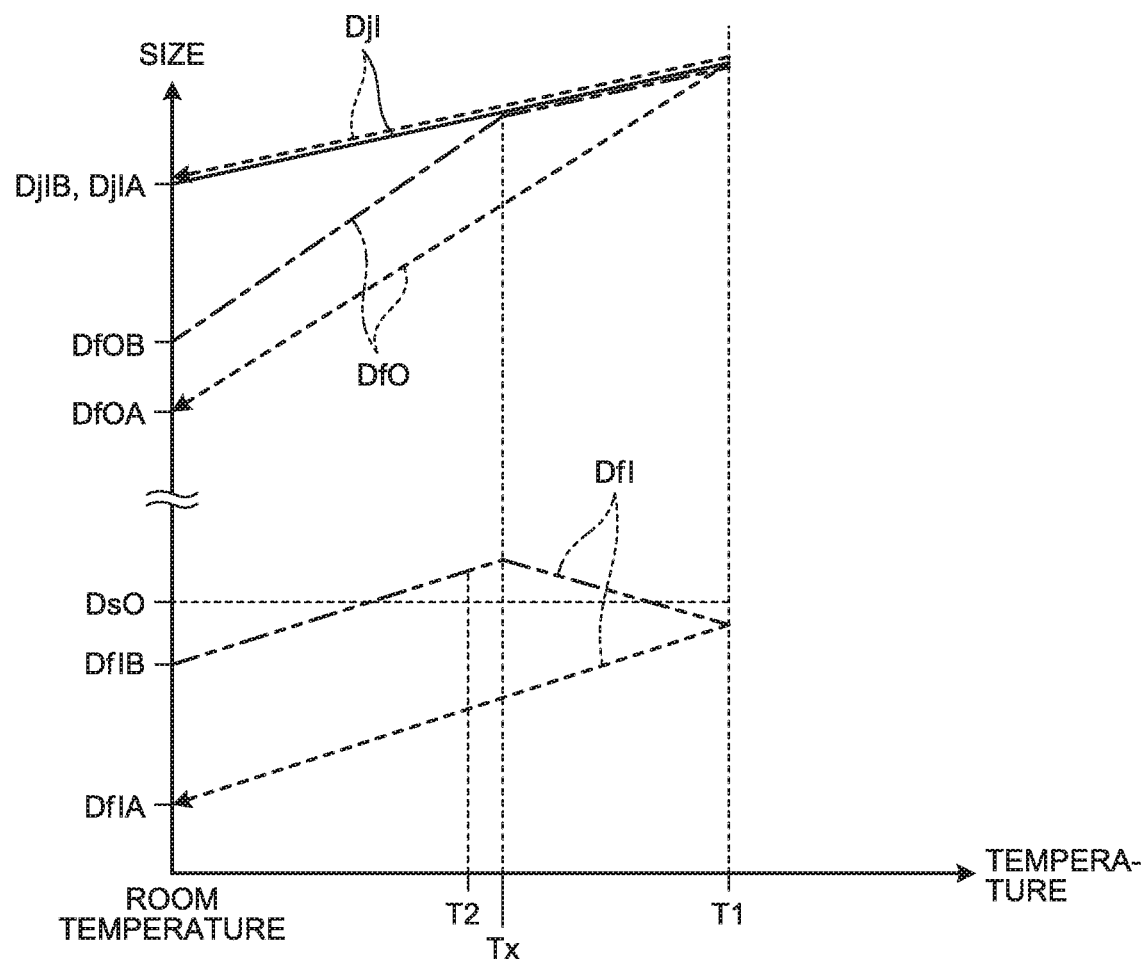
FIG. 11 is a diagram explaining an effect of the first embodiment.
Figure 12:
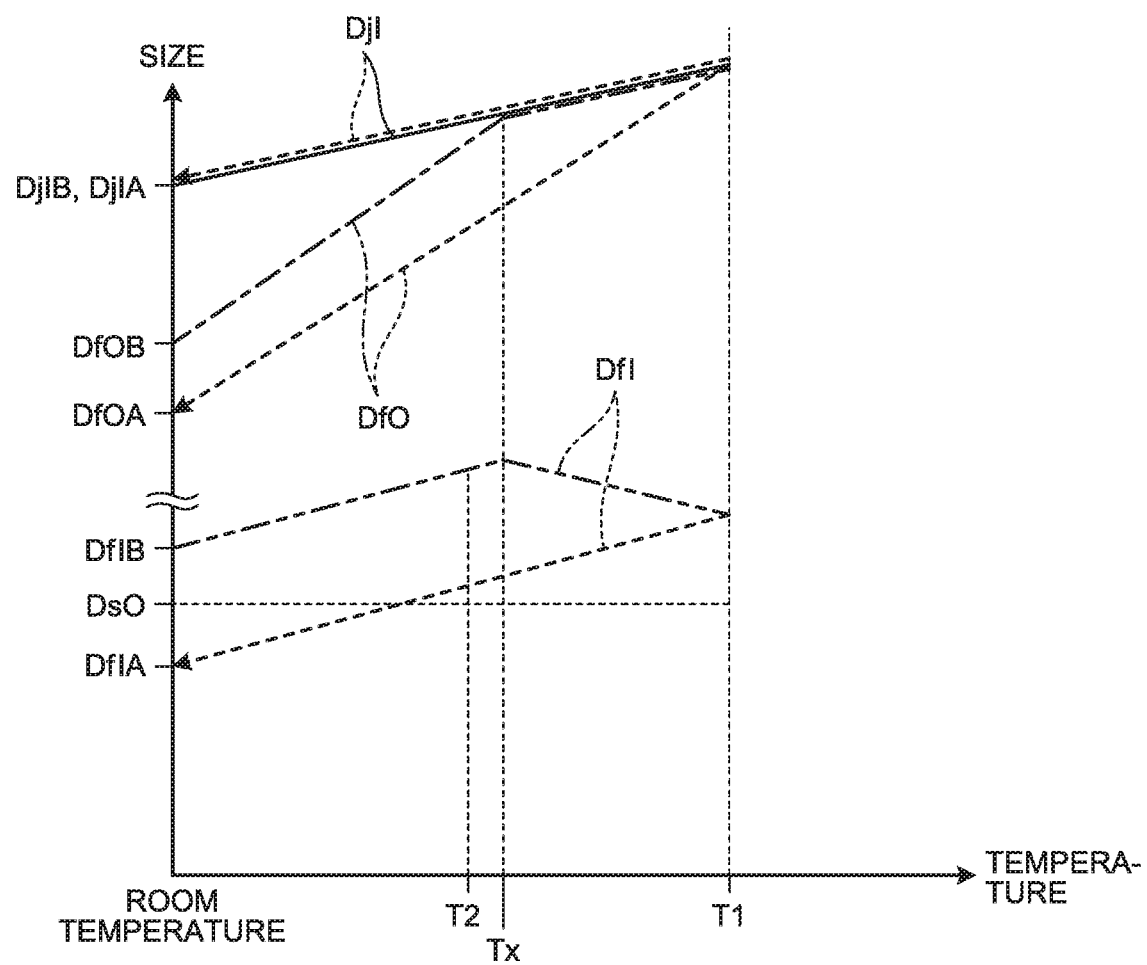
FIG. 12 is a diagram explaining an effect of the first embodiment.
Figure 13:
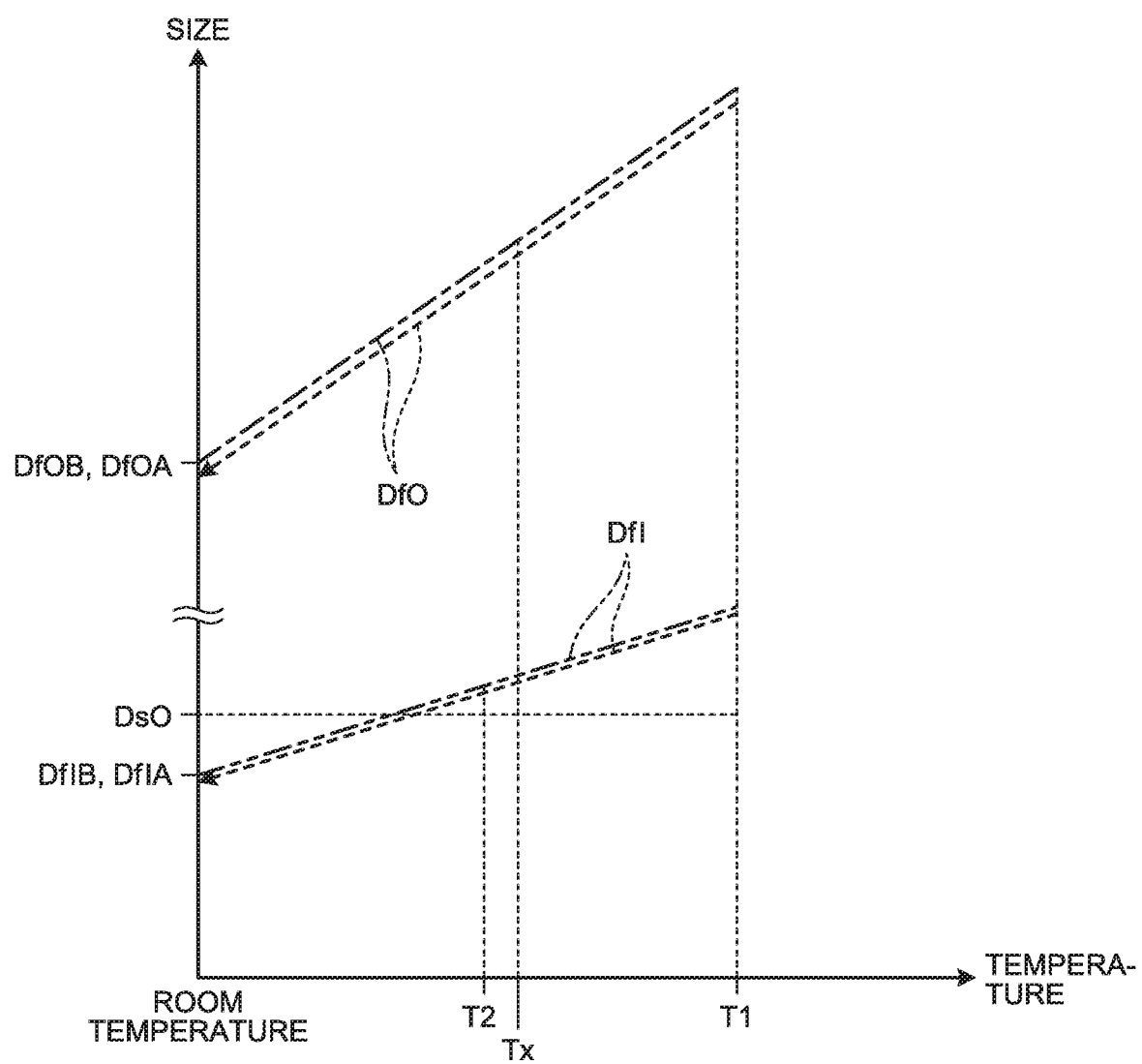
FIG. 13 is a diagram explaining an effect of the first embodiment.

FIG. 11 to FIG. 13 are diagrams explaining an effect of the first embodiment. Specifically, FIG. 11 and FIG. 12 are diagrams corresponding to FIG. 10, and are diagrams showing changes of the inner diameter Djl of the recessed portion 21, the outer diameter size DfO of the flange 102, and the inner diameter size Dfl of the joint insertion portion 1021 when the joining method shown in FIG. 4 is performed without inserting the axis member 101 in the joint insertion portion 1021 (omitting the first-member inserting step S3). Moreover, in FIG. 11, before performing the joining method (at room temperature), the outer diameter size DsO of the axis member 101 is assumed to be larger than the inner diameter size Dfl (DflB) of the joint insertion portion 1021 similarly to FIG. 10. On the other hand, in FIG. 12, before performing the joining method (at room temperature), the outer diameter size DsO of the axis member 101 is assumed to be smaller than the inner diameter size Dfl (DflB) of the joint insertion portion 1021. FIG. 13 is a diagram showing changes of the outer diameter size DfO of the flange 102 and the inner diameter size Dfl of the joint insertion portion 1021 when shrink fitting not using the first expansion-restricting member 2 is performed in the related art, without inserting the axis member 101 in the joint insertion portion 1021.

The interference indicating joint strength between the axis member 101 and the flange 102 is considered herein.

Originally, the interference can be defined by a size acquired by subtracting the inner diameter size DflB of the joint insertion portion 1021 from the outer diameter size DsO of the axis member 101 before joining (at room temperature) (size DsO−size DflB) (hereinafter, referred to as first definition). However, because the joint insertion portion 1021 is caused to have plastic deformation in a diameter shrinking direction in the first embodiment in the process of the joining method (the additional heating step S4), it is necessary to consider the interference based on a definition different from the first definition.

Specifically, the first expansion-restricting member 2 is not used in the shrink fitting in the related art. Therefore, the joint insertion portion 1021 does not make plastic deformation in the diameter shrinking direction. That is, as for the inner diameter size Dfl of the joint insertion portion 1021, the inner diameter size DflB before performing the shrink fitting in the related art is to be the same as the inner diameter size DflA after completion of the shrink fitting in the related art if the axis member 101 is not inserted in the joint insertion portion 1021 as shown in FIG. 13. Therefore, in the shrink fitting in the related art, the interference indicating the joint strength between the axis member 101 and the flange 102 can be considered based on the first definition.

On the other hand, because the first expansion-restricting member 2 is used in the joining method of the first embodiment, the joint insertion portion 1021 makes plastic deformation in the diameter shrinking direction at the additional heating step S4 (FIG. 11). That is, as for the inner diameter size Dfl of the joint insertion portion 1021, the inner diameter size DflA after completion of the joining method is to be smaller than the inner diameter size DflB before performing the joining method if the axis member 101 is not inserted in the joint insertion portion 1021 as shown in FIG. 11. Therefore, in the joining method of the first embodiment, it is necessary to apply a second definition in which the interference indicating the joint strength between the axis member 101 and the flange 102 is defined by a size acquired by subtracting the inner diameter size DflA of the joint insertion portion 1021 from the outer diameter size DsO of the axis member 101 after completion of the joining method (at room temperature).

As it is found from comparison between FIG. 11 and FIG. 13, when the axis member 101 and the flange 102 that are made from the same material and in the same dimensions are joined together by the joining method according to the first embodiment (FIG. 11) and by the shrink fitting in the related art (FIG. 13), the interference in the joining method according to the first embodiment (the second definition (size DsO−size DflA)) is larger than the interference in the shrink fitting in the related art (the first definition (size DsO−size DflB)). Therefore, by applying the joining method according to the first embodiment, joint strength between the axis member 101 and the flange 102 can be improved from that in the shrink fitting in the related art.

In the shrink fitting in the related art, if the flange 102 in which the inner diameter size DflB of the joint insertion portion 1021 is larger than the outer diameter size DsO of the axis member 101 before performing the shrink fitting (at room temperature) is used, the interference (the first definition) cannot be obtained. Therefore, the axis member 101 and the flange 102 cannot be joined together.

On the other hand, in the joining method of the first embodiment, the joint insertion portion 1021 is caused to make plastic deformation in the diameter shrinking direction at the additional heating step S4. Therefore, even if the flange 102 in which the inner diameter size DflB of the joint insertion portion 1021 is larger than the outer diameter size DsO of the axis member 101 before performing the joining method (at room temperature) as shown in FIG. 12, a sufficient interference (the second definition (size DsO−size DflA)) can be obtained. That is, the axis member 101 and the flange 102 can be joined together. Accordingly, when the interference is considered based on the first definition, the axis member 101 and the flange 102 can be joined together even when the interference (the first definition) is a negative value, and a range of the interference (the first definition) increases. That is, it is not necessary to control the processing tolerance between the axis member 101 and the flange 102 in a narrow range.

From the above, according to the joining method according to the first embodiment, an effect that a desired joint strength can be obtained while making processing management of the axis member 101 and the flange 102 easy is produced.

Second Embodiment

Next, a second embodiment of the disclosure is explained.

In the following explanation, common reference symbols are assigned to components common with the first embodiment described above, and detailed explanation thereof is omitted or simplified.

A joining method according to the second embodiment differs in a point that an additional heating step and a cooling step are performed again on a joined work subjected to joining after the axis member 101 and the flange 102 are joined together by the joining method explained in the first embodiment described above.

The joining method according to the second embodiment is explained below.

Joining Method

Figure 15A:
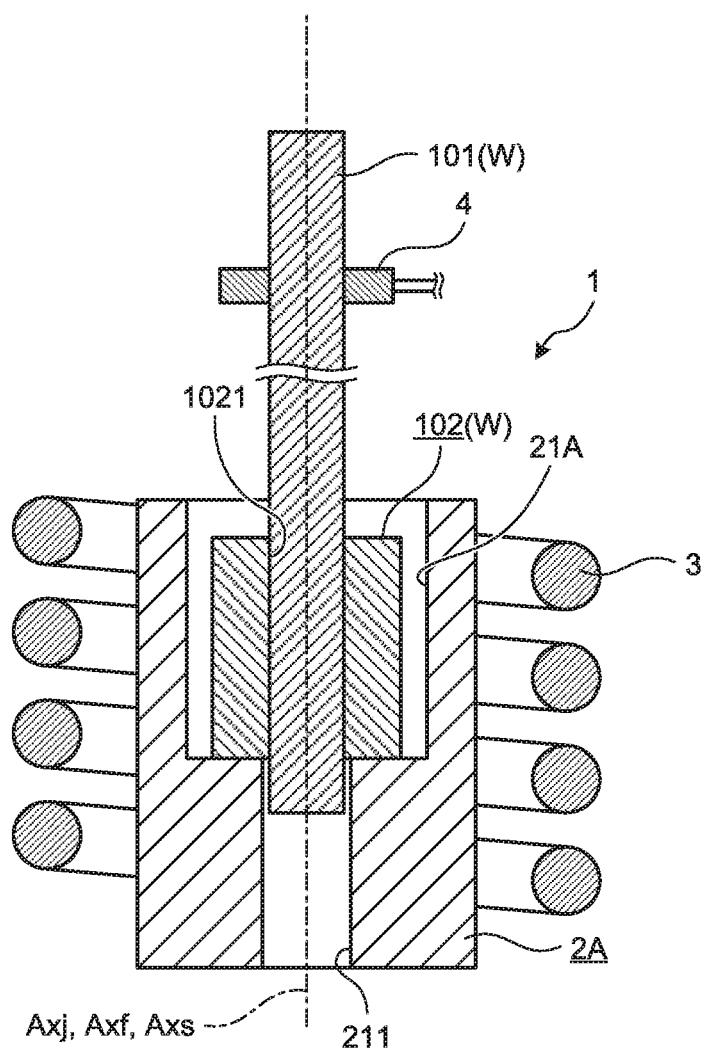
FIG. 15A is a diagram explaining the joining method shown in FIG. 14.
Figure 15B:
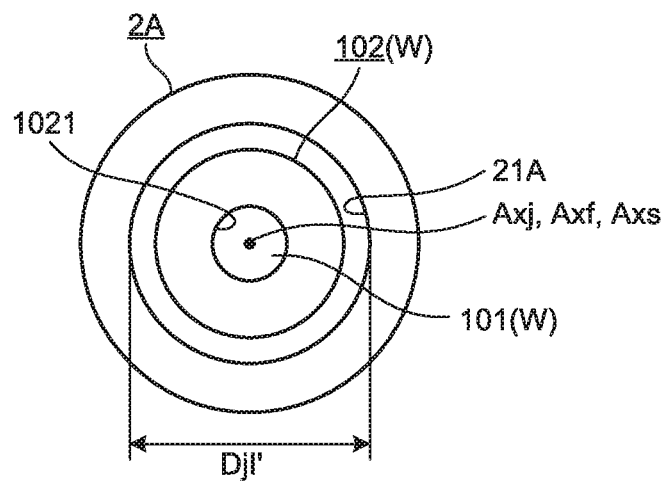
FIG. 15B is a diagram explaining the joining method shown in FIG. 14.
Figure 16A:
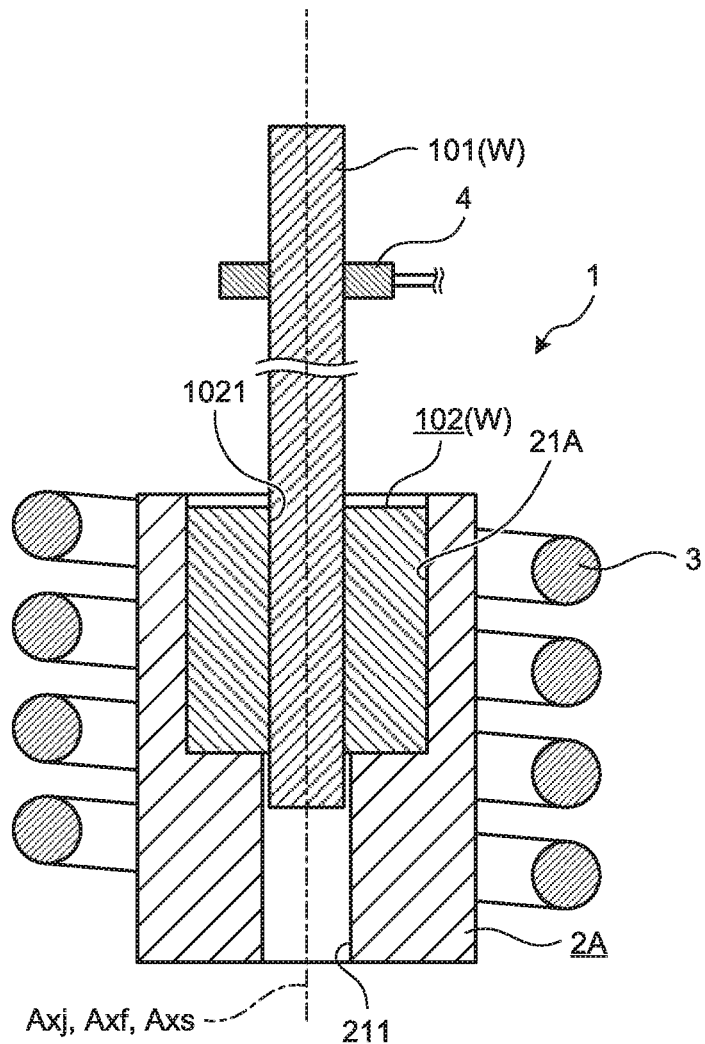
FIG. 16A is a diagram explaining the joining method shown in FIG. 14.
Figure 16B:
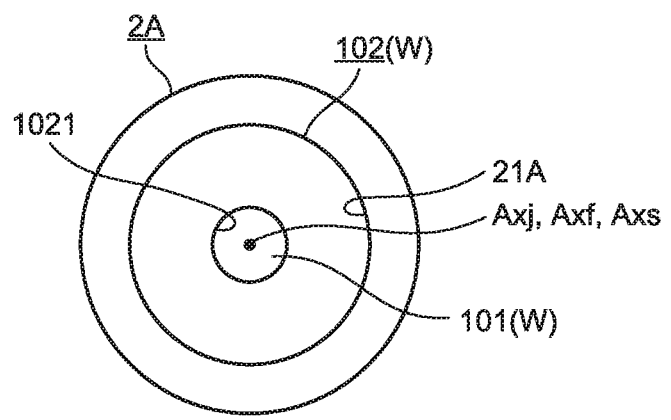
FIG. 16B is a diagram explaining the joining method shown in FIG. 14.
Figure 17A:
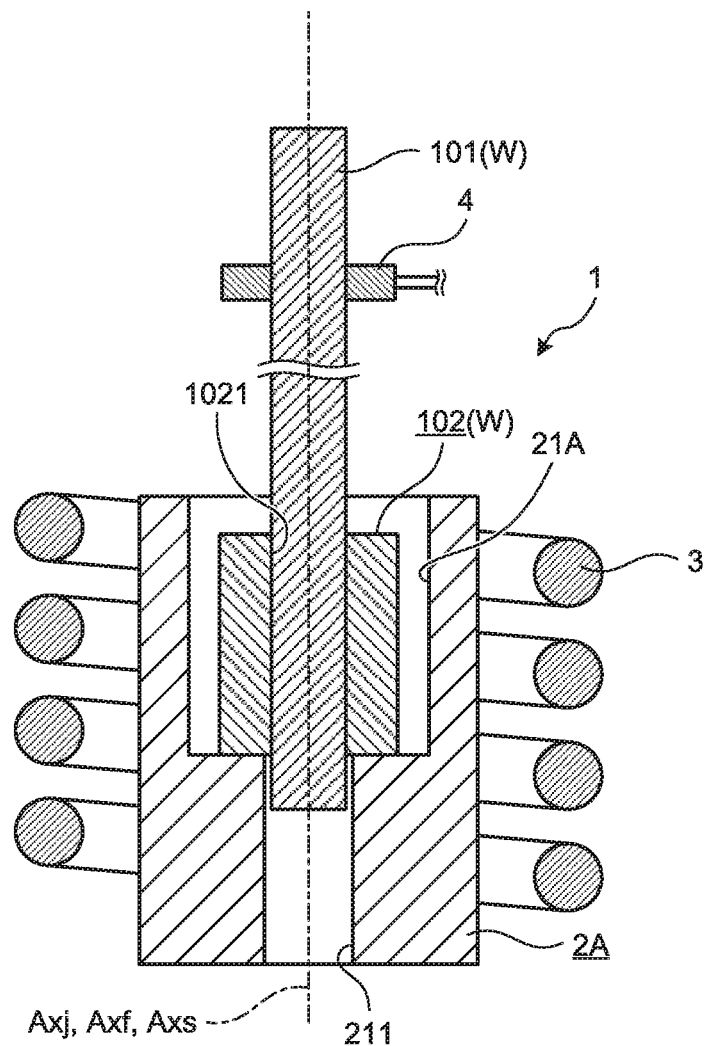
FIG. 17A is a diagram explaining the joining method shown in FIG. 14.
Figure 17B:
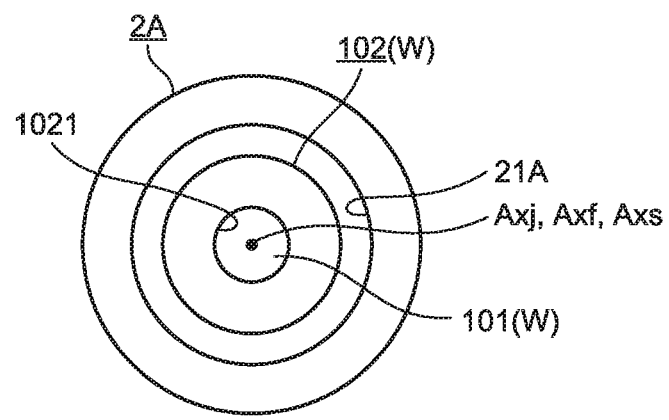
FIG. 17B is a diagram explaining the joining method shown in FIG. 14.

FIG. 14 is a flowchart showing the joining method according to the second embodiment. FIG. 15A, FIG. 15B, FIG. 16A, FIG. 16B, FIG. 17A, and FIG. 17B are diagrams explaining the joining method shown in FIG. 14. Specifically, FIG. 15A, FIG. 16A, and FIG. 17A are diagrams corresponding to FIG. 3A. FIG. 15B, FIG. 16B, and FIG. 17B are diagrams corresponding to FIG. 3B.

The joining method according to the second embodiment only differs from the joining method (FIG. 4) explained in the first embodiment described above in that steps S1A, S4A, S5A are added as shown in FIG. 14. Therefore, in the following, only steps S1A, S4A, S5A are explained sequentially.

Step S1A

Step S1A (joined-work setting step) is performed after step S5.

Specifically, an operator changes the first expansion-restricting member 2 used at steps S1 to S5 to a second expansion-restricting member 2A as shown in FIG. 15A or FIG. 15B.

The second expansion-restricting member 2A corresponds to an expansion restricting member according to the disclosure. This second expansion-restricting member 2A is made from the same material as the first expansion-restricting member 2, and is only different from the first expansion-restricting member 2 in that a recessed portion 21A (setting insertion portion according to the disclosure), an inner diameter size of which is different from recessed portion 21 is included. An inner diameter size Djl' of the recessed portion 21A (FIG. 15B) is set to be smaller than the inner diameter size Djl of the recessed portion 21 at room temperature, and be larger than the outer diameter size DfO (DfOA) of the flange 102 after performing step S5.

Moreover, the operator sets the joined work W in which the axis member 101 and the flange 102 are joined together at steps S1 to S5 in the axis-member holding unit 4 as shown in FIG. 15A. The operator operates the axis-member holding unit 4 to set the joined work W in the second expansion-restricting member 2A (the recessed portion 21A) such that the center axes Axf, Axs of the joined work W coincide with the center axis Axj of the second expansion-restricting member 2A (the recessed portion 21A) as shown in FIG. 15A or FIG. 15B. In this state, because it is room temperature and the inner diameter size Djl' of the recessed portion 21A is larger than the outer diameter size DfO (DfOA) of the flange 102 as described above, there is a gap between an inner peripheral surface of the recessed portion 21A and the outer peripheral surface of the flange 102 as shown in FIG. 15A or FIG. 15B.

Step S4A

Step S4A (additional heating step) is performed after step S1A. Specifically, the operator heats the second expansion-restricting member 2A by induction heating until the temperature of the flange 102 reaches the first temperature T1 similarly to step S4, to cause the flange 102 to have thermal expansion as shown in FIG. 16A or FIG. 16B.

The first temperature T1 at step S4A can be the same as the first temperature T1 at step S4 or can be different temperature. Specifically, the first temperature T1 at step S4A can be any temperature as long as it exceeds expansion restricting temperature at which the inner diameter size Djl' of the recessed portion 21A and the outer diameter size DfO become the same according to thermal expansion of the flange 102 and the second expansion-restricting member 2A.

As described above, the inner diameter size Djl' of the recessed portion 21A is set to be smaller than the inner diameter size Djl of the recessed portion 21. Therefore, by performing step S4A, the thermal expansion of the flange 102 is mechanically restricted by the inner peripheral surface of the second expansion-restricting member 2A (the recessed portion 21A) more strongly than at step S4. That is, a contracting force acts more on the joint insertion portion 1021.

Step S5A

Step S5A (cooling step) is performed after step S4A.

Specifically, the operator stops induction heating of the second expansion-restricting member 2A similarly to step S5, and cools the second expansion-restricting member 2A and the flange 102 to room temperature to cause the flange 102 to contract as shown in FIG. 17A or FIG. 17B. By performing this step S5A, a diameter shrinking force further acts on the joint insertion portion 1021 by the contraction of the flange 102.

According to the joining method according to the second embodiment explained above, an effect similar to that of the first embodiment described above can be obtained.

Moreover, in the joining method according to the second embodiment, the additional heating step S4A and the cooling step S5A are performed again on the joined work W obtained by joining the axis member 101 and the flange 102 together at steps S1 to S5, using the second expansion-restricting member 2A that has the recessed portion 21A of the inner diameter size Djl' that is smaller than the inner diameter size Djl of the recessed portion 21 in the first expansion-restricting member 2 used at the additional heating step S4. Therefore, a higher joint strength than the joint strength obtained at steps S1 to S5 can be obtained.

Furthermore, even if a desired joint strength has not been obtained at step S1 to S5, by improving the joint strength by the additional heating step S4A and the cooling step S5A, the desired joint strength can be obtained. Therefore, when an interference is considered based on the first definition, a range of the interference (the first definition) can be further increased. That is, it is not necessary to manage the processing tolerance of the axis member 101 and the flange 102 in a narrow range, and the processing management of the axis member 101 and the flange 102 can be further simplified.

It can be considered to perform the joining method (FIG. 4) using the second expansion-restricting member 2A in the first embodiment instead of the first expansion-restricting member 2.

In this case, because the inner diameter size Djl' of the recessed portion 21A is small, thermal expansion of the flange 102 is mechanically restricted by the inner peripheral surface of the second expansion-restricting member 2A (the recessed portion 21A) and shrink of the diameter of the joint insertion portion 1021 starts in a low heating temperature stage. As a result, the joint insertion portion 1021 cannot spread much. When the interference is considered based on the first definition, the upper limit of the interference (the first definition) on which the axis member 101 and the flange 102 can be joined becomes small. Moreover, because the inner diameter size Dfl of the joint insertion portion 1021 after cooling becomes even smaller, the lower limit of the interference (the first definition) on which the axis member 101 and the flange 102 can be joined becomes small. Consequently, even if the second expansion-restricting member 2A having the small inner diameter size Djl' of the recessed portion 21A is used, the range of the interference (the first definition) on which the axis member 101 and the flange 102 can be joined or the range of the interference (the first definition) with which a desired joint strength can be obtained is not much different from the case of using the first expansion-restricting member 2.

The range of the interference (the first definition) on which the axis member 101 and the flange 102 can be joined or the range of the interference (the first definition) with which a desired joint strength can be obtained can be made wider when the additional heating step S4A and the cooling step S5A are performed again on the joined work W obtained by joining the axis member 101 and the flange 102 together at steps S1 to S5 as in the joining method according to the second embodiment than when the joining method (FIG. 4) is performed using the second expansion-restricting member 2A instead of the first expansion-restricting member 2.

EXAMPLES

Next, an effect of the disclosure is explained based on specific examples.

Example 1

In Example 1, the axis member 101 and the flange 102 made from following materials and in following dimensions were used, and the axis member 101 and the flange 102 were joined together by the joining method (FIG. 4) explained in the first embodiment described above. Hereinafter, the joining method (FIG. 4) explained in the first embodiment described above is referred to as single joining method for convenience of explanation.

Material of the axis member 101: titanium alloy
Length of a joint portion in the axis member: 4 mm
Outer diameter size DsO of the axis member 101: 3.52 mm
Material of the flange 102: aluminum alloy (A7075)
Outer diameter size DfO of the flange 102: 6 mm
Inner diameter size DfI (DfIB) of the joint insertion portion 1021: 3.5 mm
Inner diameter size DjI of the recessed portion 21: 6.03 mm The second temperature T2 at the pre-joining heating step S2 was set to 300° C. The first temperature T1 at the additional heating step S4 was set to 450° C.

Example 2

In Example 2, except the outer diameter size DsO of the axis member 101 being 3.51 mm, the axis member 101 and the flange 102 that were structured with the same materials and in the same dimensions as Example 1 described above were used, and the axis member 101 and the flange 102 were joined together by the single joining method same as Example 1 described above.

Example 3

In Example 3, except the outer diameter size DsO of the axis member 101 being 3.50 mm, the axis member 101 and the flange 102 that were structured with the same materials and in the same dimensions as Example 1 described above were used, and the axis member 101 and the flange 102 were joined together by the single joining method same as Example 1 described above.

Example 4

In Example 4, except the outer diameter size DsO of the axis member 101 being 3.49 mm, the axis member 101 and the flange 102 that were structured with the same materials and in the same dimensions as Example 1 described above were used, and the axis member 101 and the flange 102 were joined together by the single joining method same as Example 1 described above.

Example 5

In Example 5, except the outer diameter size DsO of the axis member 101 being 3.48 mm, the axis member 101 and the flange 102 that were structured with the same materials and in the same dimensions as Example 1 described above were used, and the axis member 101 and the flange 102 were joined together by the single joining method same as Example 1 described above.

Example 6

In Example 6, the axis member 101 and the flange 102 that were structured with the same materials and in the same dimensions as Example 1 described above were used, and the axis member 101 and the flange 102 were joined together by the joining method (FIG. 14) explained in the second embodiment described above. Hereinafter, the joining method (FIG. 14) explained in the second embodiment described above is referred to as repeated joining method for convenience of explanation.

The inner diameter size DjI' of the recessed portion 21A was set to 6.01 mm. Moreover, the first temperature T1 at the additional heating step S4A was set to 450° C.

Example 7

In Example 7, the axis member 101 and the flange 102 that were structured with the same materials and in the same dimensions as Example 2 described above were used, and the axis member 101 and the flange 102 were joined together by the repeated joining method same as Example 6 described above.

Example 8

In Example 8, the axis member 101 and the flange 102 that were structured with the same materials and in the same dimensions as Example 3 described above were used, and the axis member 101 and the flange 102 were joined together by the repeated joining method same as Example 6 described above.

Example 9

In Example 9, the axis member 101 and the flange 102 that were structured with the same materials and in the same dimensions as Example 4 described above were used, and the axis member 101 and the flange 102 were joined together by the repeated joining method same as Example 6 described above.

Example 10

In Example 10, the axis member 101 and the flange 102 that were structured with the same materials and in the same dimensions as Example 5 described above were used, and the axis member 101 and the flange 102 were joined together by the repeated joining method same as Example 6 described above.

Comparative Example 1

In Comparative Example 1, the axis member 101 and the flange 102 that were structured with the same materials and in the dimensions as Example 1 described above were used, and the axis member 101 and the flange 102 were joined together by the shrink fitting without the first and the second expansion-restricting members 2, 2A in the related art.

Comparative Example 2

In Comparative Example 2, the axis member 101 and the flange 102 that were structured with the same materials and in the dimensions as Example 2 described above were used, and the axis member 101 and the flange 102 were joined together by the shrink fitting in the related art same as Comparative Example 1 described above.

Comparative Example 3

In Comparative Example 3, the axis member 101 and the flange 102 that were structured with the same materials and in the dimensions as Example 3 described above were used, and the axis member 101 and the flange 102 were joined together by the shrink fitting in the related art same as Comparative Example 1 described above.

Comparative Example 4

In Comparative Example 4, the axis member 101 and the flange 102 that were structured with the same materials and in the dimensions as Example 4 described above were used, and the axis member 101 and the flange 102 were joined together by the shrink fitting in the related art same as Comparative Example 1 described above.

Comparative Example 5

In Comparative Example 5, the axis member 101 and the flange 102 that were structured with the same materials and in the dimensions as Example 5 described above were used, and the axis member 101 and the flange 102 were joined together by the shrink fitting in the related art same as Comparative Example 1 described above.

Evaluations and Results

As an evaluation method, one out of the axis member 101 and the flange 102 joined together in Examples 1 to 10 and Comparative Examples 1 to 5 was fixed and the other one was rotated about the center axes Axf, Axs, and a force (joint strength (N·m) in a rotating direction) at which the other one came off from the one was measured, respectively. Because the measurement range of the measuring device was up to 3 N·m, the joint strength in a rotating direction equal to or higher than 3 N·m was not measured. Furthermore, the desired joint strength in a rotating direction was 3 N·m or higher. Results are as shown in Table 1 below.

TABLE 1

| | Outer diameter size of axis member | Interference (first definition) | Joining method | Joint strength in rotating direction |
|---|---|---|---|---|
| Example 1 | 3.52 mm | 0.02 mm | Single joining method | 3 N · m or higher |
| Example 2 | 3.51 mm | 0.01 mm | | 3 N · m or higher |
| Example 3 | 3.50 mm | 0 mm | | 3 N · m or higher |
| Example 4 | 3.49 mm | −0.01 mm | | 2.6 N · m |
| Example 5 | 3.48 mm | −0.02 mm | | 1.1 N · m |
| Example 6 | 3.52 mm | 0.02 mm | Repeated joining method | 3 N · m or higher |
| Example 7 | 3.51 mm | 0.01 mm | | 3 N · m or higher |
| Example 8 | 3.50 mm | 0 mm | | 3 N · m or higher |
| Example 9 | 3.49 mm | −0.01 mm | | 3 N · m or higher |
| Example 10 | 3.48 mm | −0.02 mm | | 3 N · m or higher |

TABLE 1-continued

| | Outer diameter size of axis member | Interference (first definition) | Joining method | Joint strength in rotating direction |
|---|---|---|---|---|
| Comparative example 1 | 3.52 mm | 0.02 mm | Sshrink fitting in the related art | 1.6 N · m |
| Comparative example 2 | 3.51 mm | 0.01 mm | | 1.4 N · m |
| Comparative example 3 | 3.50 mm | 0 mm | | Unable to be joined |
| Comparative example 4 | 3.49 mm | −0.01 mm | | Unable to be joined |
| Comparative example 5 | 3.48 mm | −0.02 mm | | Unable to be joined |

Results of Shrink Fitting in the Related Art

In the shrink fitting in the related art, as shown in Table 1, when the outer diameter size DsO of the axis member 101 is equal to or smaller than the inner diameter size DflB of the joint insertion portion 1021 (Comparative Examples 3 to 5), the axis member 101 and the flange 102 were not able to be joined. Moreover, in Comparative Examples 1, 2, although the axis member 101 and the flange 102 was able to be joined together, the desired joint strength in a rotating direction (3 N·m or higher) was not able to be obtained.

That is, when the interference is considered based on the first definition, a range of the interference (first definition) on which the axis member 101 and the flange 102 can be joined together in the shrink fitting in the related art is 0.01 mm to 0.02 mm.

Results of Single Joining Method

In the joining method of the disclosure, as shown in Table 1, the axis member 101 and the flange 102 were able to be joined together in all of Examples 1 to 5. However, in Examples 4, 5, although the axis member 101 and the flange 102 were able to be joined, the desired joint strength in a rotating direction (3 N·m or higher) was not able to be obtained.

That is, when the interference is considered based on the first definition, a range of the interference (first definition) on which the axis member 101 and the flange 102 can be joined together in the single joining method of the disclosure is −0.02 mm to 0.02 mm, and is wider than that in the shrink fitting in the related art. Moreover, a range of the interference (first definition) with which the desired joint strength in a rotating direction (3 N·m or higher) can be obtained is 0 mm to 0.02 mm, and is wider than that in the shrink fitting in the related art.

Results of Repeated Joining Method

In the repeated joining method of the disclosure, as shown in Table 1, the axis member 101 and the flange 102 were able to be joined together and, further, the desired joint strength in a rotating direction (3 N·m or higher) was able to be obtained in all of Examples 6 to 10.

That is, when the interference is considered based on the first definition, a range of the interference (first definition) on which the axis member 101 and the flange 102 can be joined together and with which the desired joint strength in a rotating direction (3 N·m or higher) in the repeated joining method of the disclosure is −0.02 mm to 0.02 mm. That is, the range of the interference (first definition) with which the desired joint strength in a rotating direction (3 N·m or higher) in the repeated joining method of the disclosure is wider than that in the single joining method.

Other Embodiments

Embodiments to implement the disclosure have been explained, but the disclosure is not to be limited to the embodiments described above.

The first and the second expansion-restricting members 2, 2A mechanically restrict the outer peripheral surface of the flange 102 when mechanically restricting the thermal expansion of the flange 102 in the first and the second embodiments described above, but it is not limited thereto. As long as the thermal expansion of the flange 102 can be restricted and the joint insertion portion 1021 can be caused to have plastic deformation in a direction in which the diameter shrinks, for example, a structure to mechanically restricts an upper end surface and a lower end surface of the flange 102 can be applied.

In the first and the second embodiments, the additional heating step S4 (S4A) and the cooling step S5 (S5A) can be performed on a joined work (for example, the axis member 101 and the flange 102 joined together in Comparative Examples 1, 2) subjected to the shrink fitting in the related art, by using the joining apparatus 1. A joining method in which an additional heating step and a cooling step are performed on a joined work subjected to the shrink fitting in the related art as described above is also included in the disclosure.

In the first and the second embodiments described above, materials of the axis member 101, the flange 102, and the first and the second expansion-restricting members 2, 2A are not limited to the materials explained in the first and the second embodiments described above. As long as the condition that the linear expansion coefficient $\beta$ of the first and the second expansion-restricting members 2, 2A is smaller than the linear expansion coefficient $\alpha$ of the flange 102 is satisfied, any material can be used as materials to form the first and the second expansion-restricting members 2, 2A and the flange 102.

Furthermore, for the second expansion-restricting member 2A, as long as the structure provides strong mechanical restriction to the thermal expansion of the flange 102 compared to the first expansion-restricting member 2, a structure with a different material (linear expansion coefficient) and different dimensions from the first expansion-restricting member 2 can be applied.

The first-member inserting step S3 is performed after the flange 102 reaches the second temperature T2 in the first and the second embodiments, but it is not limited thereto. The first-member inserting step S3 can be performed at any time as long as the inner diameter size Dfl of the joint insertion portion 1021 is larger than the outer diameter size DsO of the axis member 101 as a result of the thermal expansion of the flange 102. That is, the first-member inserting step S3 can be performed at the pre-joining heating step S2 or at the additional heating step S4.

As a means to heat the flange 102, the electromagnetic-induction heating coil 3 is used in the first and the second embodiments described above, but it is not limited thereto. A structure of directly or indirectly heating the flange 102 by a method other than the electromagnetic induction can also be applied.

The additional heating step and the cooling step are repeated twice in the second embodiment described above, but it is not limited thereto, and they can be repeated three or more times. In this case, as explained in the second embodiment described above, in the additional heating step in a later stage, an expansion restricting member is changed sequentially to one having a stronger mechanical restriction to the thermal expansion of the flange 102 than that in the additional heating step in an earlier stage.

Figure 18:
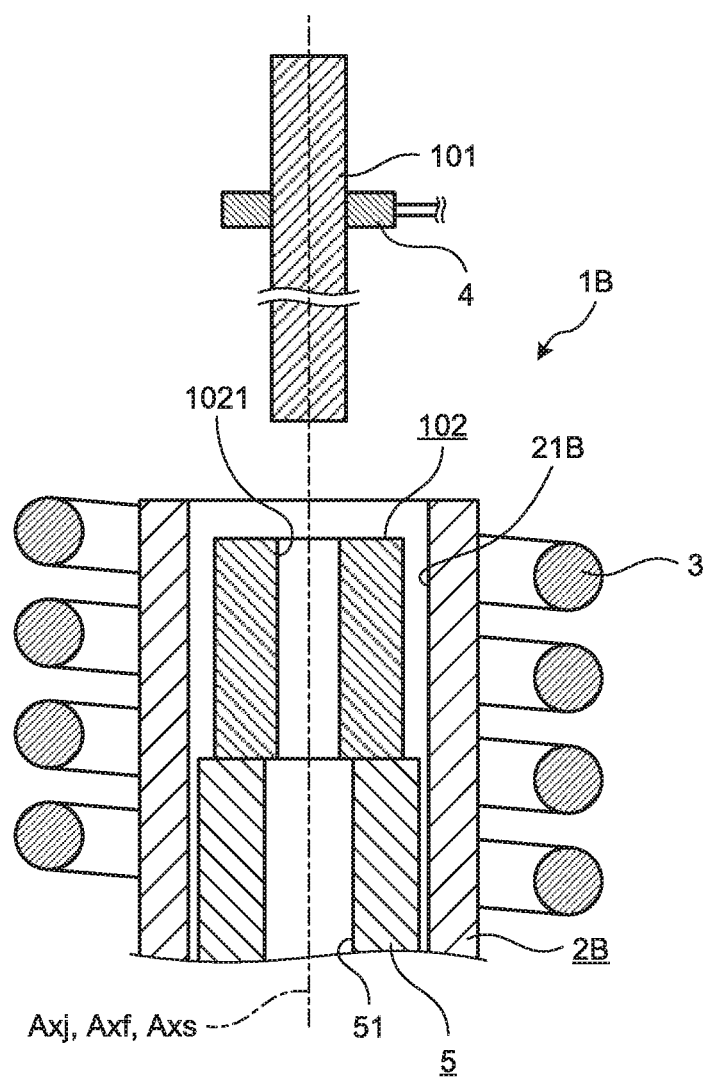
FIG. 18 is a diagram showing a modification of the first and the second embodiments.

FIG. 18 is a diagram showing a modification of the first and the second embodiments. Specifically, FIG. 18 is a diagram corresponding to FIG. 3A.

Instead of the joining apparatus 1 explained in the first and the second embodiments described above, a joining apparatus 1B shown in FIG. 18 can be used.

The joining apparatus 1B according to the present modification includes, as shown in FIG. 18, an expansion restricting member 2B and a platform 5 in addition to the electromagnetic-induction heating coil 3 and the axis-member holding unit 4 explained in the first and the second embodiments described above.

The expansion restricting member 2B differs from the first and the second expansion-restricting members 2, 2A explained in the first embodiment described above only in a point that the recessed portions 21, 21A are pierced through to a lower end.

A portion in which the recessed portions 21, 21A are pierced through to the lower end is a portion that mechanically restricts the thermal expansion of the flange 102 with the inner peripheral surface, and corresponds to a setting insertion portion 21B according to the disclosure.

The platform 5 corresponds to the bottom portion of the recessed portions 21, 21A in the first and the second expansion-restricting members 2, 2A explained in the first embodiment described above, and is a portion on which the flange 102 is set. The platform 5 has an insertion hole 51 corresponding to the insertion hole 211 formed at the bottom portion of the recessed portions 21, 21A.

Figure 19A:
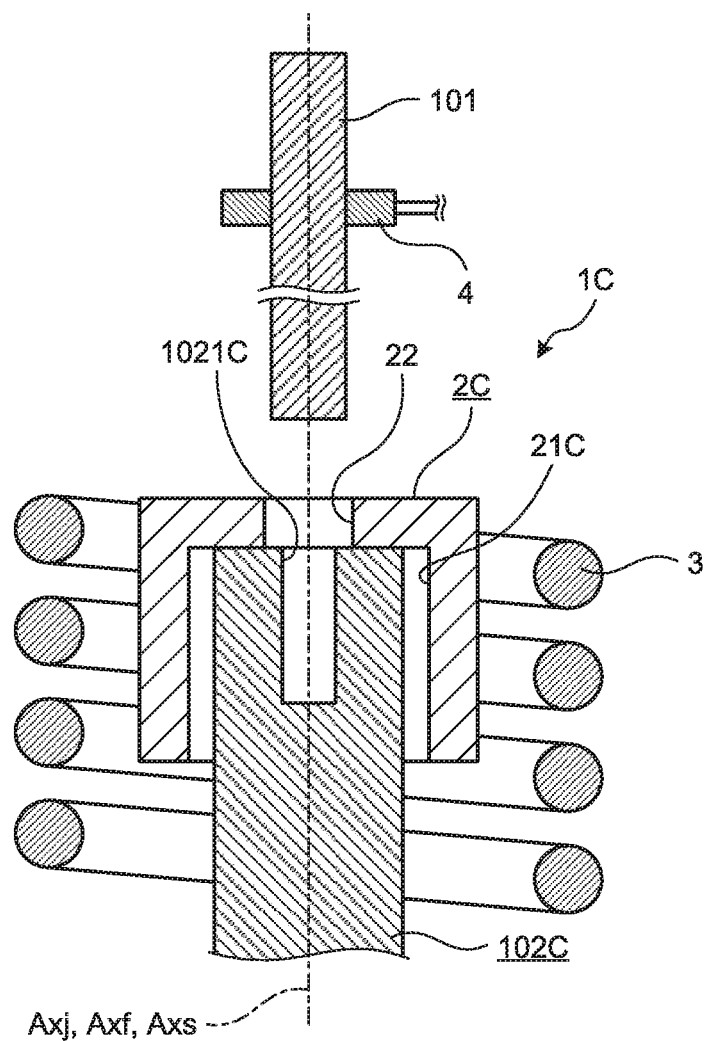
FIG. 19A is a diagram showing a modification of the first and the second embodiment.
Figure 19B:
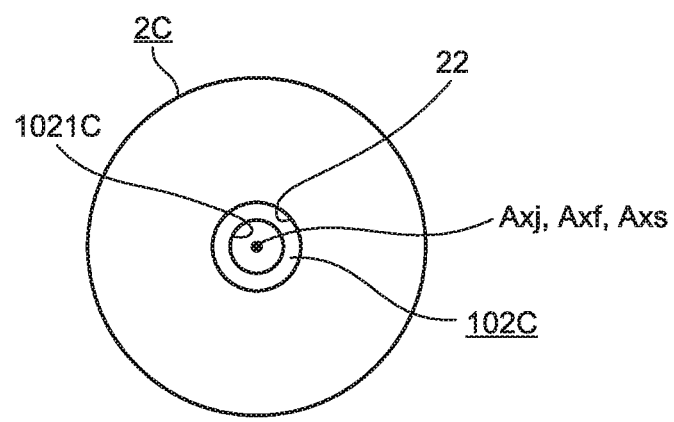
FIG. 19B is a diagram showing the modification of the first and the second embodiment.

FIG. 19A and FIG. 19B are diagrams showing a modification of the first and the second embodiments. Specifically, FIG. 19A is a diagram corresponding to FIG. 3A. FIG. 19B is a diagram corresponding to FIG. 3B.

Instead of the flange 102 explained in the first and the second embodiments described above, a flange 102C shown in FIG. 19A or FIG. 19B can be used.

The flange 102C according to the present modification differs from the flange 102 explained in the first and the second embodiments described above only in a point that the joint insertion portion 1021 is structured with a recessed portion 1021C not piercing through to a bottom end. The recessed portion 1021C is a portion in which the axis member 101 is inserted, and corresponds to a joint insertion portion according to the disclosure.

Moreover, when the flange 102C is applied, a joining apparatus 1C shown in FIG. 19A or FIG. 19B can be used instead of the joining apparatus 1 explained in the first and the second embodiments described above.

The joining apparatus 1C according to the present modification includes, as shown in FIG. 19A or 19B, an expansion restricting member 2C in addition to the electromagnetic-induction heating coil 3 and the axis-member holding unit 4 explained in the first and the second embodiments described above.

The expansion restricting member 2C has a bottomed cylindrical shape as shown in FIG. 19A. The expansion restricting member 2C is set to direct its bottom upward and to cover an upper end portion of the flange 102C. That is, an inner surface of the expansion restricting member 2C is a portion that mechanically restricts the thermal expansion of the flange 102C similarly to the recessed portions 21, 21A of the first and the second expansion-restricting members 2, 2A explained in the first embodiment described above, and corresponds to a setting insertion portion 21C according to the disclosure.

Furthermore, in a bottom portion of the expansion restricting member 2C, a setting insertion hole 22 that pierces through the expansion restricting member 2C between inside and outside thereof, to insert the axis member 101 from the outside of the expansion restricting member 2C to the inside.

According to some embodiments, an effect that a desired joint strength can be obtained with easy processing control of subjects to be joined is produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A joining method of joining two pieces of subjects to be joined together,
    the subjects being a first member and a second member that has a joint insertion portion in which the first member is inserted,
    the method comprising:
    heating the second member that is set in an expansion restricting member including in a joining apparatus and in which the first member is inserted to the joint insertion portion to a first temperature to cause the second member to have thermal expansion and thereby causing the joint insertion portion to have plastic deformation in a direction in which a diameter shrinks with mechanically restricting thermal expansion of the second member by an inner surface of the expansion restricting member; and
    wherein the second member is heated after the first member is inserted into the second member and after both the first and second members are inserted into the expansion restricting member; and
    after heating both the first and second members,
    cooling the second member to join the first member to the second member.

2. The joining method according to claim 1, wherein
    the heating and the cooling are repeatedly performed more than one time while sequentially changing the expansion restricting member to one having stronger mechanical restriction to thermal expansion of the second member.

3. The joining method according to claim 2, wherein
    the expansion restricting member includes a setting insertion portion in which the second member is inserted, and is configured to mechanically restrict thermal expansion of the second member with an inner surface of the setting insertion portion at the heating, and
    the heating and the cooling are repeatedly performed more than one time while changing the expansion restricting member to one in which an inner diameter size of the setting insertion portion is smaller.

4. The joining method according to claim 1, wherein a linear expansion coefficient of the expansion restricting member is smaller than a linear expansion coefficient of the second member.

5. The joining method according to claim 1, wherein
    the plastic deformation at the heating is plastic deformation that occurs when the second member is heated to the first temperature to:
        continue the thermal expansion of the second member further after the second member comes into contact with the inner surface of the expansion restricting member due to the thermal expansion of the second member; and
        cause the joint insertion portion of the second member whose outward thermal expansion is restricted by coming into contact with the inner surface of the expansion restricting member to have deformation in a direction in which an inner diameter of the joint insertion portion reduces.

6. The joining method according to claim 5, wherein a clearance is formed between the inner surface of the expansion restricting member and an outer surface of the second member to allow the thermal expansion of the second member.

7. The joining method according to claim 6, wherein
    the expansion restricting member includes a setting insertion portion in which the second member is inserted, and is configured to mechanically restrict thermal expansion of the second member with an inner surface of the setting insertion portion at the heating, and
    the joining method further comprising:
    inserting the second member in the setting insertion portion in a state keeping a gap between the setting insertion portion and an outer surface of the second member;
    preheating the second member to second temperature that is lower than the first temperature after the inserting to cause the second member to have thermal expansion; and
    inserting the first member in the joint insertion portion, the inserting of the first member being performed at a timing selected from, at the preheating, after the pre heating, and at the heating, wherein
    the heating is performed after the preheating.

8. The joining method according to claim 5, wherein
    the expansion restricting member includes a setting insertion portion in which the second member is inserted, and is configured to mechanically restrict thermal expansion of the second member with an inner surface of the setting insertion portion at the heating, and
    the joining method further comprising:
    inserting the second member in the setting insertion portion in a state keeping a gap between the setting insertion portion and an outer surface of the second member;
    preheating the second member to second temperature that is lower than the first temperature after the inserting to cause the second member to have thermal expansion; and
    inserting the first member in the joint insertion portion, the inserting of the first member being performed at a timing selected from, at the preheating, after the pre heating, and at the heating, wherein
    the heating is performed after the preheating.

9. The joining method according to claim 1, wherein a clearance is formed between the inner surface of the expansion restricting member and an outer surface of the second member to allow the thermal expansion of the second member.

10. The joining method according to claim 9, wherein
    the expansion restricting member includes a setting insertion portion in which the second member is inserted, and is configured to mechanically restrict thermal expansion of the second member with an inner surface of the setting insertion portion at the heating, and the joining method further comprising:
inserting the second member in the setting insertion portion in a state keeping a gap between the setting insertion portion and an outer surface of the second member;
preheating the second member to second temperature that is lower than the first temperature after the inserting to cause the second member to have thermal expansion; and
inserting the first member in the joint insertion portion, the inserting of the first member being performed at a timing selected from, at the preheating, after the pre heating, and at the heating, wherein
the heating is performed after the preheating.

11. The joining method according to claim 1, wherein the expansion restricting member includes a setting insertion portion in which the second member is inserted, and is configured to mechanically restrict thermal expansion of the second member with an inner surface of the setting insertion portion at the heating, and
the joining method further comprising:
inserting the second member in the setting insertion portion in a state keeping a gap between the setting insertion portion and an outer surface of the second member;
preheating the second member to a second temperature that is lower than the first temperature after the inserting to cause the second member to have thermal expansion; and
inserting the first member in the joint insertion portion, the inserting of the first member being performed at a timing selected from, at the preheating, after the pre heating, and at the heating, wherein
the heating is performed after the preheating.

* * * * *